(12) United States Patent
Bosua et al.

(10) Patent No.: US 11,284,820 B1
(45) Date of Patent: *Mar. 29, 2022

(54) ANALYTE DATABASE ESTABLISHED USING ANALYTE DATA FROM A NON-INVASIVE ANALYTE SENSOR

(71) Applicant: Know Labs, Inc., Seattle, WA (US)

(72) Inventors: Phillip Bosua, Seattle, WA (US); Ronald Erickson, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/201,508

(22) Filed: Mar. 15, 2021

(51) Int. Cl.
| | | |
|---|---|---|
| *A61B 5/145* | (2006.01) | |
| *A61B 5/00* | (2006.01) | |
| *A61B 5/1455* | (2006.01) | |
| *A61B 5/0507* | (2021.01) | |

(52) U.S. Cl.
CPC .......... *A61B 5/1455* (2013.01); *A61B 5/0022* (2013.01); *A61B 5/0507* (2013.01); *A61B 5/14532* (2013.01); *A61B 5/14546* (2013.01); *A61B 5/681* (2013.01); *A61B 5/7275* (2013.01); *A61B 2503/40* (2013.01)

(58) Field of Classification Search
CPC ... A61B 5/1455; A61B 5/0022; A61B 5/0507; A61B 5/14532; A61B 5/14546; A61B 5/681; A61B 5/7275; A61B 2503/40
USPC ......................................................... 600/310
See application file for complete search history.

(56) References Cited

U.S. PATENT DOCUMENTS

| 4,202,000 | A | | 5/1980 | Carballes | |
|---|---|---|---|---|---|
| 6,005,520 | A | * | 12/1999 | Nalbandian | H01Q 1/38 343/700 MS |
| 7,295,827 | B2 | | 11/2007 | Liu et al. | |
| 8,223,021 | B2 | | 7/2012 | Goodnow et al. | |

(Continued)

FOREIGN PATENT DOCUMENTS

| JP | 2012125382 | 7/2012 |
|---|---|---|
| KR | 1020160081740 | 7/2016 |

(Continued)

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320, 2020 (11 pages).

(Continued)

*Primary Examiner* — Daniel L Cerioni
*Assistant Examiner* — Deirdre M Willgohs
(74) *Attorney, Agent, or Firm* — Hamre, Schumann, Mueller & Larson, P.C.

(57) ABSTRACT

Establishing an analyte database using analyte data that has been obtained using one or more non-invasive analyte sensors, and using the analyte database to analyze data obtained using a non-invasive analyte sensor. Once the analyte database is established, the analyte database can be updated with new analyte data, and the analyte database can be used to analyze the new analyte data to derive information from the new analyte data. For example, in the case of a human target, the new analyte data together with the analyte database can be used to predict an actual or possible abnormal medical pathology of the human target.

7 Claims, 14 Drawing Sheets

(56) References Cited

U.S. PATENT DOCUMENTS

| | | | |
|---|---|---|---|
| 9,198,607 | B2 | 12/2015 | Fischer |
| 9,864,024 | B2 | 1/2018 | Vester |
| 10,149,629 | B2 | 12/2018 | Szczepaniak et al. |
| 10,405,785 | B2 * | 9/2019 | Ho .................... A61B 5/6815 |
| 10,478,101 | B1 | 11/2019 | Cespedes et al. |
| 10,548,503 | B2 * | 2/2020 | Bosua ................ A61B 5/0507 |
| 10,932,698 | B2 * | 3/2021 | Leath ................ A61B 5/14532 |
| 2001/0005183 | A1 * | 6/2001 | Nevermann ........... H01Q 5/378 |
| | | | 343/909 |
| 2003/0036713 | A1 | 2/2003 | Bouton et al. |
| 2004/0065158 | A1 | 4/2004 | Schrepfer et al. |
| 2004/0127777 | A1 | 7/2004 | Ruchti et al. |
| 2004/0133086 | A1 | 7/2004 | Ciurczak et al. |
| 2004/0235536 | A1 | 11/2004 | Kim et al. |
| 2009/0213025 | A1 * | 8/2009 | Coupez ................ H01Q 13/04 |
| | | | 343/807 |
| 2009/0275814 | A1 | 11/2009 | Watanabe et al. |
| 2010/0041969 | A1 | 2/2010 | Beise |
| 2011/0028814 | A1 | 2/2011 | Petersen et al. |
| 2014/0213870 | A1 | 7/2014 | Hsu et al. |
| 2016/0051171 | A1 | 2/2016 | Pikov et al. |
| 2017/0095667 | A1 | 4/2017 | Yakovlev et al. |
| 2017/0181658 | A1 * | 6/2017 | Dettmann ........... A61B 5/14503 |
| 2018/0028824 | A1 | 2/2018 | Pivonka et al. |
| 2019/0008422 | A1 | 1/2019 | Leath et al. |
| 2019/0053741 | A1 | 2/2019 | Chaudhry |
| 2019/0104939 | A1 | 4/2019 | Costantine et al. |
| 2019/0179008 | A1 | 6/2019 | Tavassolian et al. |
| 2019/0353752 | A1 | 11/2019 | Lin et al. |
| 2019/0357800 | A1 | 11/2019 | Bosua |
| 2019/0388000 | A1 | 12/2019 | Costantine et al. |
| 2020/0057163 | A1 | 2/2020 | Bromberg |
| 2020/0146584 | A1 | 5/2020 | Bosua |
| 2020/0187791 | A1 | 6/2020 | Leabman |
| 2020/0187792 | A1 | 6/2020 | Leabman |
| 2020/0187793 | A1 | 6/2020 | Leabman |
| 2020/0187812 | A1 | 6/2020 | Leabman |
| 2020/0187813 | A1 | 6/2020 | Leabman |
| 2020/0187814 | A1 | 6/2020 | Leabman |
| 2020/0187815 | A1 | 6/2020 | Leabman |
| 2020/0187816 | A1 | 6/2020 | Leabman |
| 2020/0187817 | A1 | 6/2020 | Leabman |
| 2020/0187818 | A1 | 6/2020 | Leabman |
| 2020/0187819 | A1 | 6/2020 | Leabman |
| 2020/0187820 | A1 | 6/2020 | Leabman |
| 2020/0187836 | A1 | 6/2020 | Leabman |
| 2020/0187837 | A1 | 6/2020 | Leabman |
| 2020/0187867 | A1 | 6/2020 | Leabman |
| 2020/0191909 | A1 | 6/2020 | Leabman |
| 2020/0191932 | A1 | 6/2020 | Leabman |
| 2020/0191933 | A1 | 6/2020 | Leabman |
| 2020/0191944 | A1 | 6/2020 | Leabman |
| 2020/0191945 | A1 | 6/2020 | Leabman |
| 2020/0191947 | A1 | 6/2020 | Leabman |
| 2020/0192426 | A1 | 6/2020 | Leabman |
| 2020/0192427 | A1 | 6/2020 | Leabman |
| 2020/0192428 | A1 | 6/2020 | Leabman |
| 2020/0193326 | A1 | 6/2020 | Leabman |
| 2020/0195197 | A1 | 6/2020 | Leabman |
| 2020/0195293 | A1 | 6/2020 | Leabman |
| 2020/0375549 | A1 | 12/2020 | Wexler et al. |

FOREIGN PATENT DOCUMENTS

| | | |
|---|---|---|
| WO | 2017163245 | 9/2017 |
| WO | 2019071138 | 4/2019 |
| WO | 2019198567 | 10/2019 |
| WO | 2019217461 | 11/2019 |
| WO | 2020006077 | 1/2020 |
| WO | 2020037171 | 2/2020 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, dated Aug. 23, 2019, 9 pages.

Qiang et al., "Quantitative detection of glucose level based on radiofrequency patch biosensor combined with volume-fixed structures," Biosensors and Bioelectronics 98:357-363, 2017.

U.S. Appl. No. 17/123,932, titled "Non-Invasive Analyte Sensor and System With Decoupled Transmit and Receive Antennas," filed Dec. 16, 2020 (49 pages).

U.S. Appl. No. 17/123,947, titled "Non-Invasive Detection of an Analyte Using Decoupled Transmit and Receive Antennas," filed Dec. 16, 2020 (46 pages).

U.S. Appl. No. 17/123,961, titled "Non-Invasive Analyte Sensor and System With Decoupled and Inefficient Transmit and Receive Antennas," filed Dec. 16, 2020 (48 pages).

U.S. Appl. No. 17/123,977, titled "Non-Invasive Detection of an Analyte Using Decoupled and Inefficient Transmit and Receive Antennas," filed Dec. 16, 2020 (47 pages).

U.S. Appl. No. 17/123,992, titled "Non-Invasive Analyte Sensor Device," filed Dec. 16, 2020 (47 pages).

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

International Search Report and Written Opinion issued for International Patent Application No. PCT/IB2020/062222, dated Mar. 25, 2021, 7 pages.

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

Mankowska, A. et al., "Association of C-Reactive Protein and Other Markers of Inflammation with Risk of Complications in Diabetic Subjects," The Journal Of The International Federation Of Clinical Chemistry And Laboratory Medicine, Mar. 2006, 17(1), pp. 8-11.

Mahendran, Y. et al., "Association of Ketone Body Levels With Hyperglycemia and Type 2 Diabetes in 9,398 Finnish Men," Diabetes, Oct. 2013, 62(10), pp. 3618-3626.

Nall, R., "Alcoholic Liver Cirrhosis," Healthline, Updated on Sep. 17, 2018, URL: https://www.healthline.com/health/alcoholic-liver-cirrhosis (Retrieved on May 3, 2021), 4 pages.

Allin, K. et al., "Elevated C-reactive protein in the diagnosis, prognosis, and cause of cancer," Abstract, Crit Rev Clin Lab Sci., Jul.-Aug. 2011, 48(4), 1 page (Retrieved from URL: https://pubmed.ncbi.nlm.nih.gov/22035340/ on May 5, 2021).

"Luteinizing Hormone (LH) Levels Test," MedlinePlus, URL: https://medlineplus.gov/lab-tests/luteinizing-hormone-lh-levels-test/ (Retrieved on May 5, 2021), 6 pages.

U.S. Appl. No. 17/201,480, titled "Analyte Database Established Using Analyte Data From Non-Invasive Analyte Sensors," filed Mar. 15, 2021 (62 pages).

U.S. Appl. No. 17/201,495, titled "Analyte Database Established Using Analyte Data From Non-Invasive Analyte Sensors," filed Mar. 15, 2021 (61 pages).

* cited by examiner

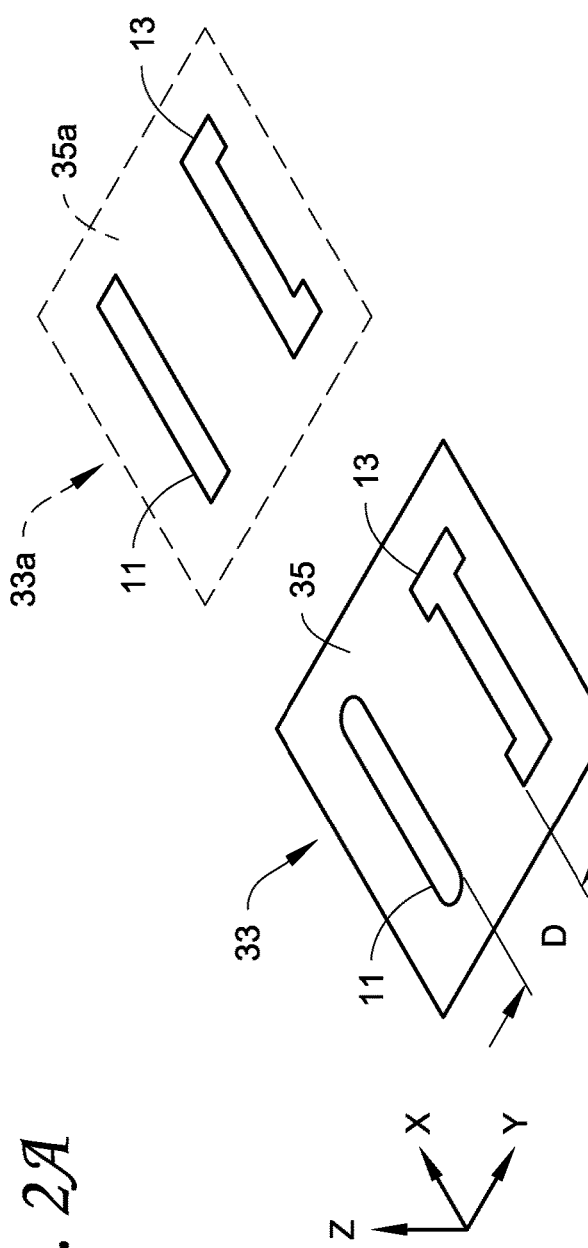
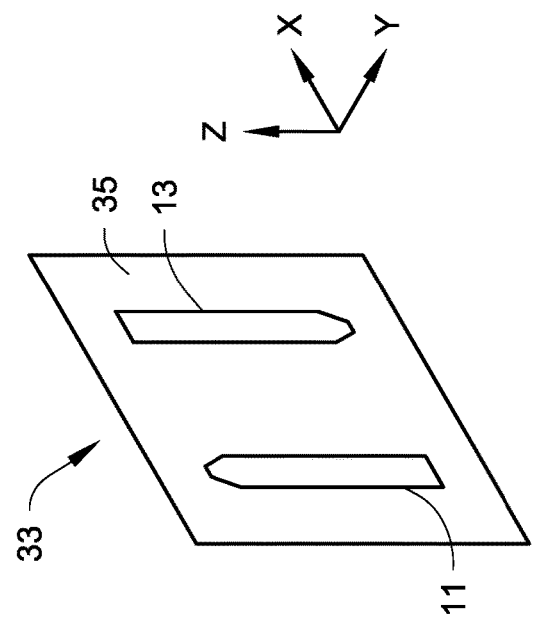
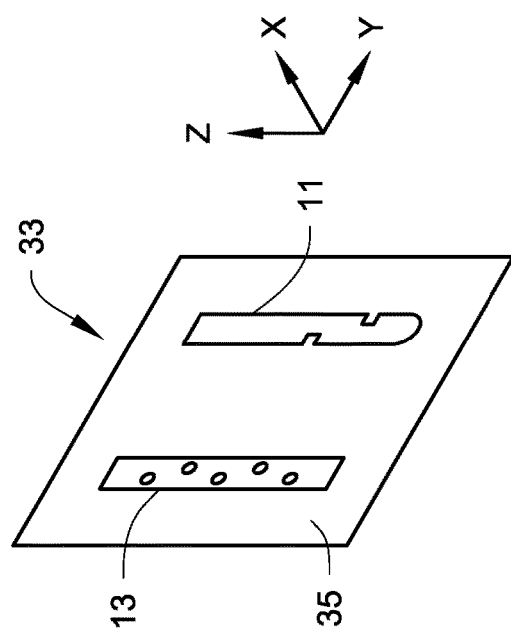
Fig. 2A
Fig. 2B
Fig. 2C

ANALYTE DATABASE ESTABLISHED USING ANALYTE DATA FROM A NON-INVASIVE ANALYTE SENSOR

FIELD

This technical disclosure relates to apparatus, systems and methods of establishing an analyte database using analyte data that has been obtained using one or more non-invasive analyte sensors, and using the analyte database to analyze data obtained using a non-invasive analyte sensor.

BACKGROUND

A sensor that uses radio or microwave frequency bands of the electromagnetic spectrum for non-invasive collection of analyte data of a subject is disclosed in U.S. Pat. No. 10,548,503. Additional examples of sensors that purport to be able to use radio or microwave frequency bands of the electromagnetic spectrum to detect an analyte in a person are disclosed in U.S. Patent Application Publication 2019/0008422 and U.S. Patent Application Publication 2020/0187791.

SUMMARY

This disclosure relates generally to establishing an analyte database using analyte data that has been obtained using non-invasive analyte sensor(s), and using the analyte database to analyze data obtained using a non-invasive analyte sensor. Once the analyte database is established, the analyte database can be updated with new analyte data, and the analyte database can be used to analyze the new analyte data to derive information from the new analyte data.

The analyte data used to establish the analyte database is obtained over a period of time from a plurality of human or animal subjects (or collectively subjects), from a plurality of animate or inanimate materials, or from a plurality of other objects. The human or animal subjects, the animate or inanimate materials, and any other objects from which analyte data is obtained using the non-invasive analyte sensors may collectively be referred to as targets. The targets used to establish the analyte database are similar to one another. For example, the targets can be humans; the targets can be the same kind of animal such as cows (or breed of cows); the targets can be the same kind of trees (such as apple trees) or the same kind of fluid such as fuel, oil, hydraulic fluid, edible or potable liquids, or the like.

In another embodiment, analyte data used to establish the analyte database is obtained over a period of time from a single target so that the analyte database is specific to a single target. Additional analyte data can then be obtained from the target, the analyte database updated with the additional analyte data.

The term "analyte" used herein refers to a substance whose constituents are being identified and/or measured. For example, glucose is a sugar that is a component of many carbohydrates. The analyte is present in a host which can be a liquid, gas, solid, gel, and combinations thereof.

The analyte data stored in the analyte database may be raw, unprocessed data that is obtained by the analyte sensor. The raw, unprocessed data may then be analyzed to extract out data on the analyte such as the presence of the analyte and/or a concentration of the analyte. The analyte data stored in the analyte database may alternatively be processed data regarding the analyte such as the presence of the analyte and/or a concentration of the analyte. The analyte data stored in the database may also be a combination of raw, unprocessed data and processed data. Regardless of the form of the analyte data stored in the analyte database, the analyte data contains information on at least one analyte in the targets. In an example where the targets are human or animal subjects, the analyte may be an indicator of an abnormal (or normal) medical pathology of the subjects. In an example where the targets are animate or inanimate materials, the analyte may be an indicator of an abnormal (or normal) condition of the materials such as, but not limited to, a contaminant or other impurity in the materials, a disease condition of the materials, a mineral in soil, and many others.

The analyte data used to establish the analyte database is collected over a period of time that is sufficient to eliminate or minimize the effects of temporary variations or aberrations in the analyte of the targets. This helps to ensure that an accurate actual or possible abnormal (or normal) indicator in the subsequently obtained analyte data can be determined based on the analyte database. The time period may vary based on a number of factors including, but not limited to, the target, the analyte being detected, temporal factors (for example time of day, the day(s) of the week, month or year), and other factors.

The time period over which the analyte data is collected can be measured in hours, days, months or even years. In one embodiment, the time period can be selected to minimize or avoid collecting analyte data encompassing natural or non-abnormal variations in the analyte of the target that may occur and that may not indicate an actual or possible abnormal condition. In another embodiment, the time period that is selected may include collecting analyte data that encompasses natural or normal variations in the analyte of the target that may occur whether or not the collected analyte data indicates an actual or possible abnormal condition.

The analyte data is collected using non-invasive analyte sensors that detect an analyte in the target via spectroscopic techniques using non-optical frequencies such as in the radio or microwave frequency range of the electromagnetic spectrum or optical frequencies in the visible range of the electromagnetic spectrum. In one embodiment, the analyte sensors described herein can be used for in vivo detection of the analyte data or used for in vitro detection of the analyte data from the target.

In one embodiment, data may also be collected from the target using a second sensor where the data from the second sensor together with the analyte data collected by the analyte sensor, can be used to predict an actual or possible abnormal (or normal) condition of the target.

In one embodiment, the techniques described herein can be used on human or animal subjects for determining an abnormal (or alternatively a normal) medical pathology. For example, in one embodiment, a method described herein can include establishing an analyte database that is based on analyte data that has been obtained from subjects by non-invasive analyte sensors that conducted a plurality of analyte sensing routines on the subjects to obtain the analyte data from the subjects over a period of time including, but not limited to, at least twenty four hours, the analyte data containing information on at least one analyte in the subjects, where the at least one analyte is an indicator of an abnormal medical pathology. Each non-invasive analyte sensor includes a detector array having at least one transmit element and at least one receive element, and for each sensing routine of the plurality of sensing routines the at least one transmit element is positioned and arranged to transmit an electromagnetic transmit signal into the corresponding subject, and the at least one receive element is positioned and arranged to detect a response resulting from transmission of the electromagnetic transmit signal by the at least one transmit element into the corresponding subject. A transmit circuit is electrically connectable to the at least one transmit element, where the transmit circuit is configured to generate the electromagnetic transmit signal to be transmitted by the at least one transmit element, and the electromagnetic transmit signal is in a radio frequency or visible range of the electromagnetic spectrum. In addition, a receive circuit is electrically connectable to the at least one receive element, where the receive circuit is configured to receive the response detected by the at least one receive element.

Once the analyte database is established, new analyte data can be obtained from a subject by a non-invasive analyte sensor. The analyte database can be updated based on the new analyte data, and the new analyte data can be analyzed based on the analyte database.

In another embodiment, analyte data obtained over a period of time from a single target using one or more of the analyte sensors described herein can be used to establish an analyte database whereby the analyte database is specific to a single target. Additional analyte data can then be obtained from the target, the analyte database updated with the additional analyte data.

In another embodiment, an analytics system described herein can include the analyte database and at least one of the non-invasive analyte sensors.

DRAWINGS

FIG. 1 is a schematic depiction of an analyte sensor system with a non-invasive analyte sensor relative to a target according to an embodiment.

FIGS. 2A-C illustrate different example orientations of antenna arrays that can be used in an embodiment of a sensor system described herein.

Like reference numbers represent like parts throughout.

DETAILED DESCRIPTION

Figure 1:
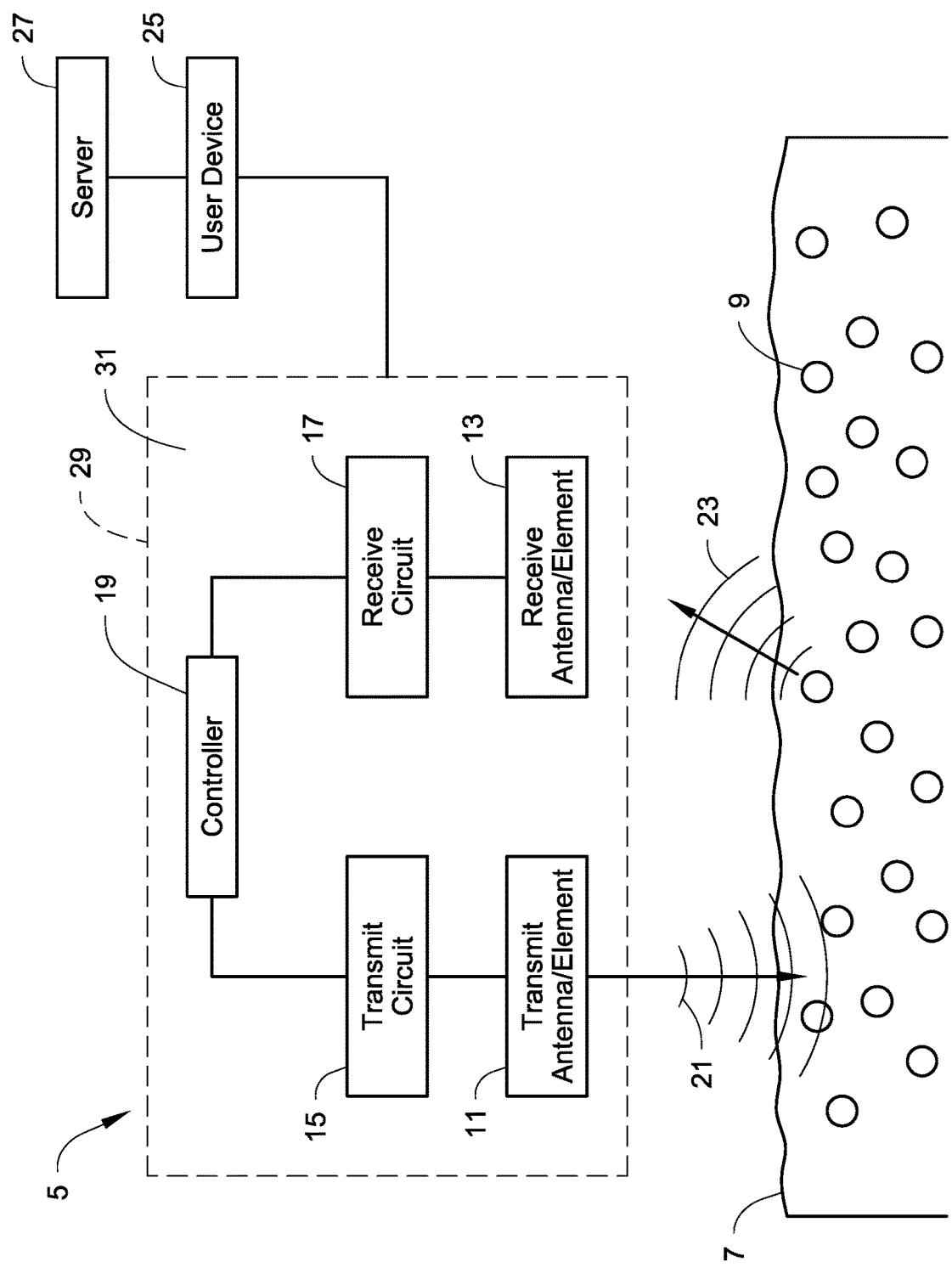

The following is a detailed description of using analyte data that has been collected from targets (or from a single target) by analyte sensors, for example non-invasive analyte sensors, to establish an analyte database and using the analyte database to analyze data obtained from a target using an analyte sensor, for example a non-invasive analyte sensor. Once the analyte database is established, the analyte database can be updated with new analyte data that is collected, and the analyte database can be used to analyze the new analyte data to derive information from the new analyte data. The information can be used to predict or derive an actual or possible condition (abnormal or normal) of the target.

The analyte data stored in the analyte database may be raw, unprocessed data that is obtained by the analyte sensor(s). Raw unprocessed data is data that is obtained by the analyte sensor(s) and that is not processed by the analyte sensor(s) and that does not undergo any other processing prior to being stored in the analyte database. The raw, unprocessed data may then be analyzed to extract out data on the analyte such as the presence of the analyte and/or a concentration of the analyte. The analyte data stored in the analyte database may alternatively be processed data regarding the analyte such as the presence of the analyte and/or a concentration of the analyte, where the processed data results from processing of raw unprocessed data by the analyte sensor(s) and/or by another device prior to being stored in the analyte database. The analyte data stored in the database may also be a combination of raw, unprocessed data and processed data.

The analyte data used to establish the analyte database is obtained over a period of time from a plurality of targets or from a single target. The targets can be human or animal subjects (or collectively subjects), a plurality of animate or inanimate materials, or a plurality of other objects. The targets used to establish the analyte database are similar to one another. For example, the targets can be humans; the targets can be the same kind of animal such as dogs (or breed of dogs); the targets can the same kind of trees (such as apple trees) or the same kind of fluid such as fuel, oil, hydraulic fluid, edible or potable liquids, or the like.

The analyte data that is collected contains information on at least one analyte in the targets. In an example where the targets are human or animal subjects, the analyte may be an indicator of an abnormal (or normal) medical pathology of the subjects. In an example where the targets are animate or inanimate materials, the analyte may be an indicator of an abnormal (or normal) condition of the materials such as, but not limited to, a contaminant or other impurity in the materials, a disease condition of the materials, a mineral in soil, and many others conditions.

The analyte data, both for establishing the analyte database and subsequent analyte data for updating the database and for analyzing, may be collected using non-invasive analyte sensors that detect an analyte in the targets via spectroscopic techniques using non-optical frequencies such as in the radio or microwave frequency range of the electromagnetic spectrum or optical frequencies in the visible range of the electromagnetic spectrum. The analyte sensors described herein can be used for in vivo detection of the analyte and in vitro detection of the analyte.

One or more analytes can be detected. The analyte(s) that is detected is an indicator of a condition (abnormal or normal) of the target. For example, when the target is a human, the analyte can be an indicator of an abnormal medical pathology of the human target. For example, the analyte can include, but is not limited to, one or more of glucose, ketones, C-reactive proteins, alcohol, white blood cells, luteinizing hormone or any other analyte that is an indicator of an actual or possible abnormal medical pathology of the human target. The abnormal medical pathology can include, but is not limited to, pre-diabetes, diabetes, cancer, cirrhosis and other medical pathologies that can be predicted based on one or more detectable analytes from the human target.

The time period over which the analyte data (both for establishing the analyte database and subsequent analyte data collection) is collected may vary based on a number of factors including, but not limited to, the target, the analyte being detected, temporal factors (for example time of day, the day(s) of the week, month or year), and other factors. The time period over which the analyte data is collected can be measured in hours, days, months or even years. In one embodiment, the time period can be selected to minimize or avoid collecting analyte data encompassing natural or non-abnormal variations in the analyte of the target(s) that may occur and that may not indicate an actual or possible abnormal (or normal) condition of the target. In another embodiment, the time period that is selected may include collecting analyte data that encompasses natural or normal variations in the analyte of the targets that may occur that may not indicate an actual or possible abnormal condition.

In one embodiment, data may also be collected from the target(s) using a second sensor where the data from the second sensor, together with the analyte data collected by the analyte sensor(s), can be used to predict an actual or possible condition of the target. In another embodiment, analyte data may also be collected from one or more additional targets and the collected analyte data of each target may be used to predict an actual or possible condition of the respective target.

Figure 6:
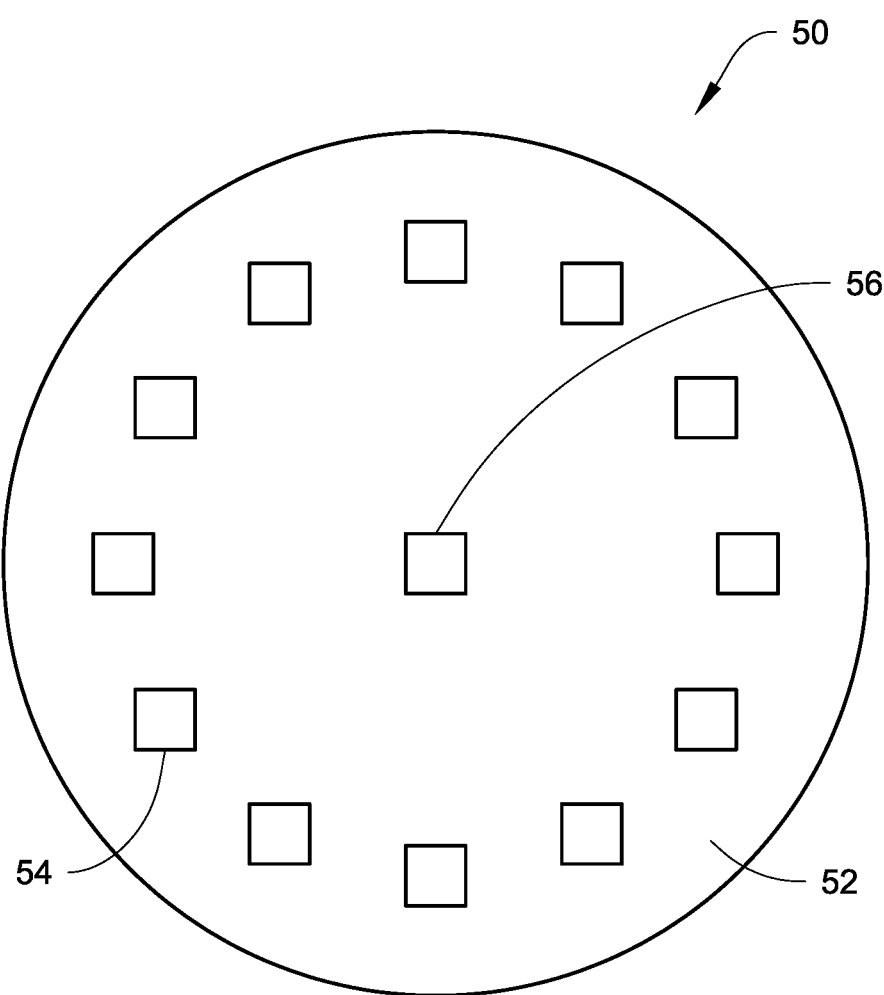
FIG. 6 is a schematic depiction of a portion of another embodiment of an analyte sensor system with an analyte sensor that uses electromagnetic energy in the form of light to perform analyte sensing described herein.
Figure 7:
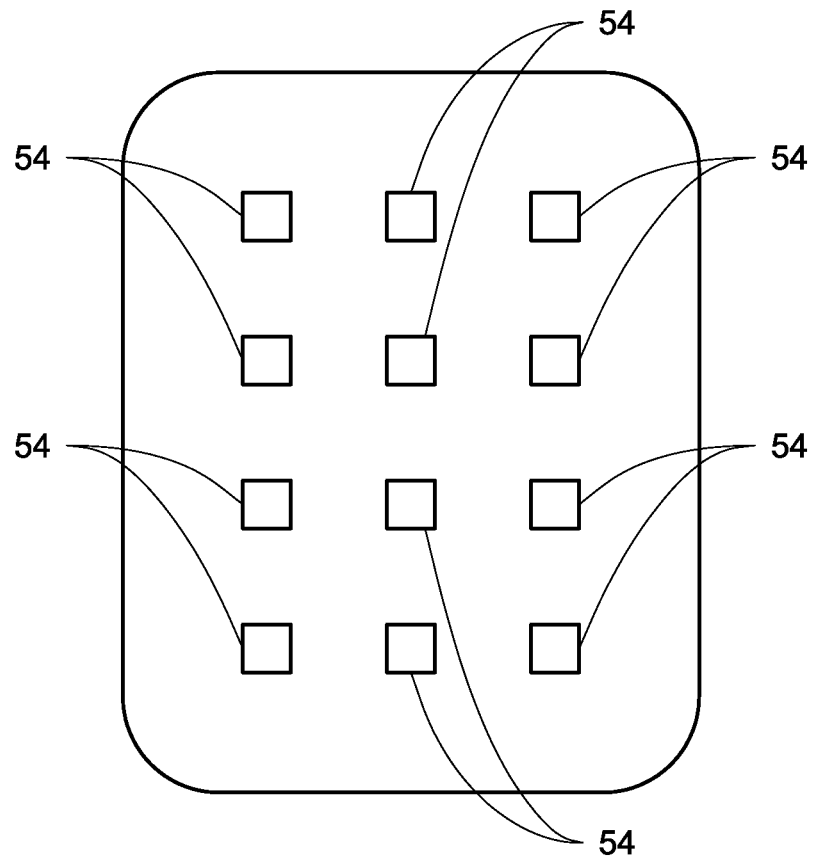
FIG. 7 illustrates another example of an analyte sensor system with an analyte sensor that uses electromagnetic energy in the form of light to perform analyte sensing described herein.
Figure 8:
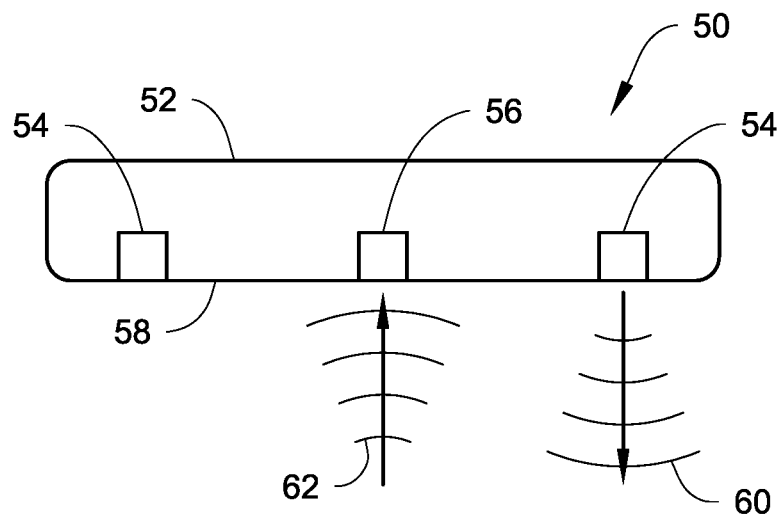
FIG. 8 depicts an example operation of the sensor system of FIG. 6.

The analyte(s) may be detected via spectroscopic techniques using non-optical frequencies such as in the radio or microwave frequency bands of the electromagnetic spectrum or optical frequencies in the visible range of the electromagnetic spectrum. An analyte sensor described herein includes a detector array having at least one transmit element and at least one receive element. The transmit element and the receive element can be antennas (FIGS. 1-5) or light emitting elements such as light emitting diodes (FIGS. 6-8). In the following description, the transmit element and the receive element, whether they are antennas or light emitting diodes, may each be referred to as a detector element.

Figure 9:
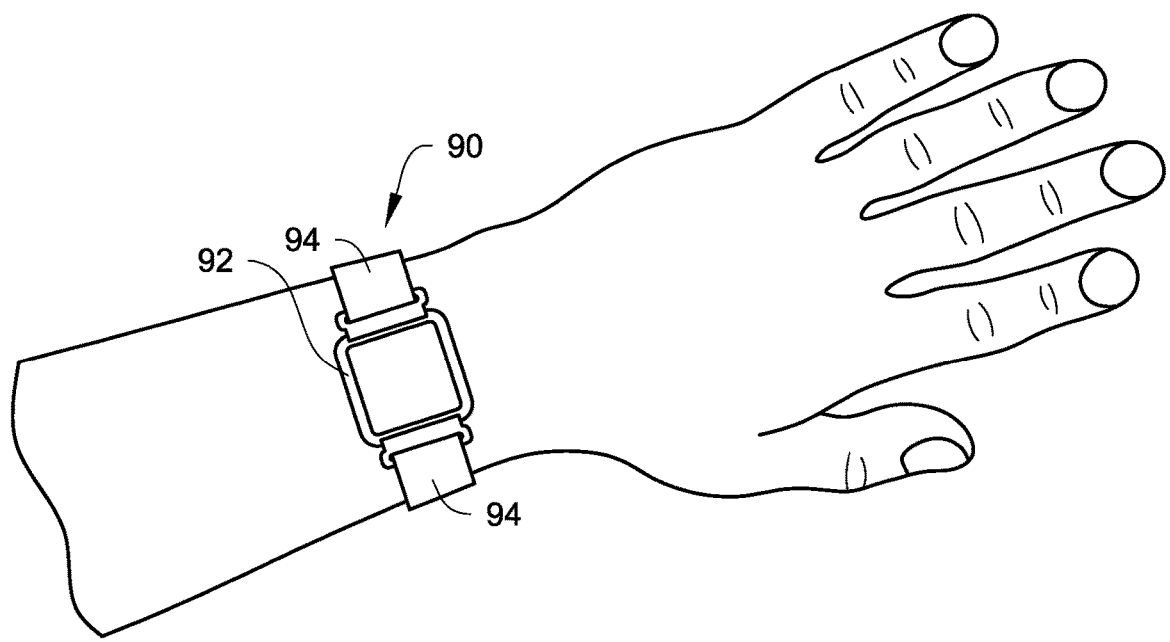
FIG. 9 illustrates another embodiment of an analyte sensor system with a non-invasive analyte sensor according to an embodiment.
Figure 10:
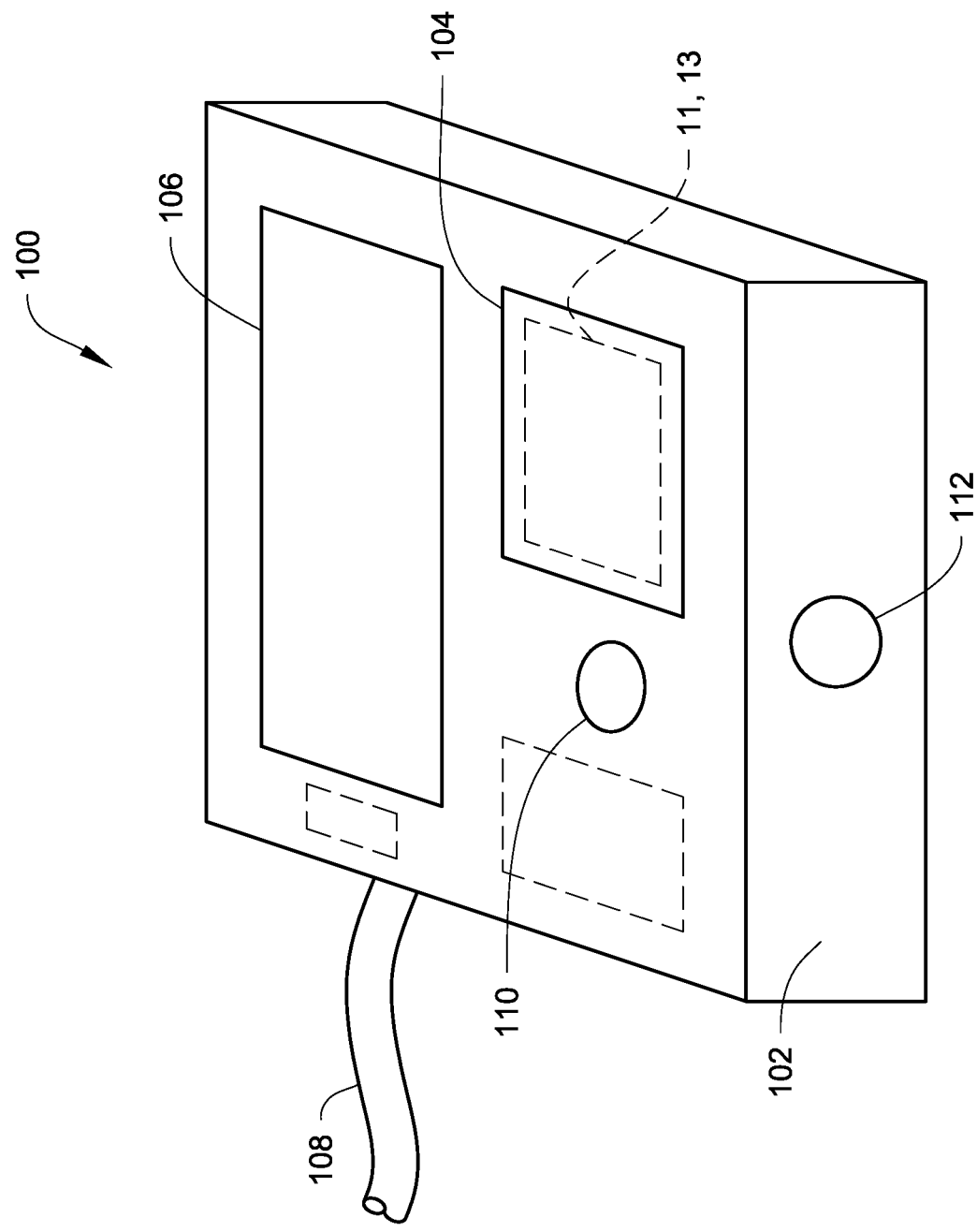
FIG. 10 illustrates another embodiment of an analyte sensor system with a non-invasive analyte sensor according to an embodiment.
Figure 11:
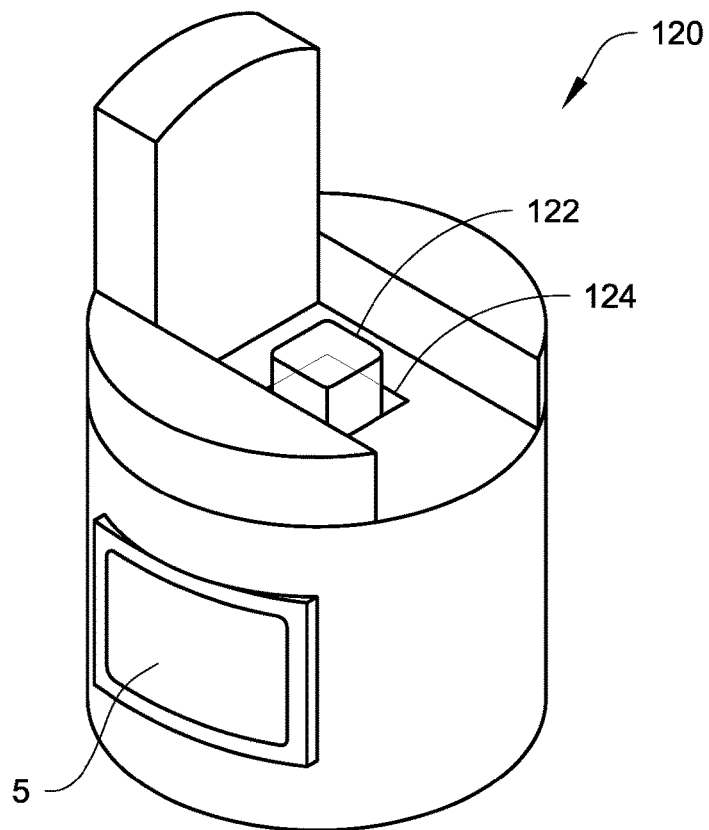
FIG. 11 illustrates another embodiment of an analyte sensor system with a non-invasive analyte sensor relative to a target according to an embodiment.
Figure 12:
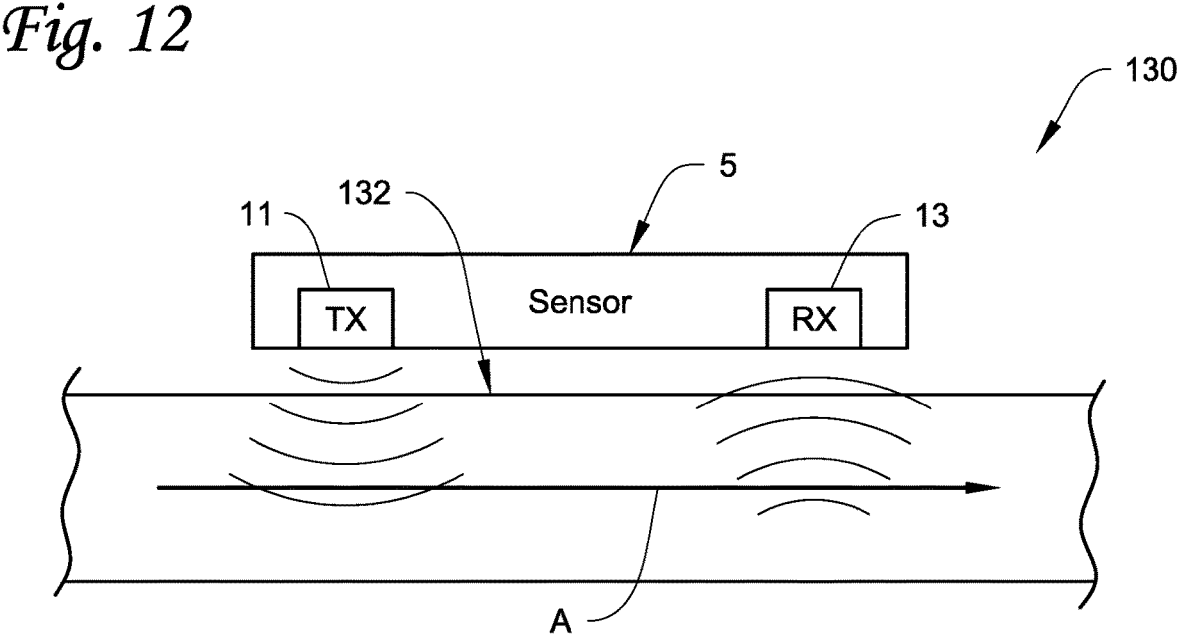
FIG. 12 illustrates another embodiment of an analyte sensor system with a non-invasive analyte sensor relative to a target according to an embodiment.

The following description together with FIGS. 1-5 will initially describe the analyte sensor system as including a detector array having two or more antennas. Later in the following description, together with FIGS. 6-8, the analyte sensor system is described as including a detector array that includes two or more light emitting devices such as light emitting diodes (LEDs). The detector array having two or more LEDs may also be described as an LED array. FIG. 9 illustrates an analyte sensor system with a non-invasive analyte sensor in the form of a body wearable sensor, for example worn around the wrist. FIG. 10 illustrates an analyte sensor system with a non-invasive analyte sensor in the form of a tabletop device. FIG. 11 illustrates an analyte sensor system with a non-invasive analyte sensor in the form of an in vitro sensor used with in vitro targets. FIG. 12 illustrates an analyte sensor system with a non-invasive analyte sensor that can be used with industrial processes.

For sake of convenience, the following description may describe the target(s) as being a human or animal subject, and the condition of the subject as being an abnormal medical pathology of the subject. However, the targets are not limited to human or animal subjects, and the condition is not limited to abnormal medical pathologies. The targets can be any objects from which one or more analytes can be detected using the analyte sensors described herein. In addition, the condition that is predicted can be any normal or abnormal condition of an object. Additional examples of conditions can include, but are not limited to, the presence or absence of a contaminant or other impurity in the target which may be a gas, liquid, solid, gel, and combinations thereof; a disease condition or lack of a disease condition of the target; a mineral or lack of mineral in soil; and many others.

In one embodiment, the presence of at least one analyte in a target can be detected. In another embodiment, an amount or a concentration of the at least one analyte in the target can be determined. The target can be any target containing at least one analyte of interest that one may wish to detect and which indicates an actual or possible abnormal or normal condition, such as an abnormal medical pathology. The target can be a human or animal. In another embodiment, an analyte can be detected from a non-human or non-animal subject, for example a plant or tree, and the detected analyte can indicate an abnormal condition of the target, for example a disease in the case of a plant or tree. The analyte can be detected from a fluid, for example blood, interstitial fluid, cerebral spinal fluid, lymph fluid or urine; human tissue; animal tissue, plant tissue, an inanimate object, soil, genetic material, or a microbe.

The detection by the sensors described herein can be non-invasive meaning that the sensor remains outside the target, such as the human body, and the detection of the analyte occurs without requiring removal of fluid or other removal from the target, such as the human body. In the case of sensing in the human body, this non-invasive sensing may also be referred to as in vivo sensing. In other embodiments, the sensors described herein may be an in vitro sensor where the target containing the analyte has been removed from its host, for example from a human body.

The analyte(s) can be any analyte that one may wish to detect that may indicate an actual or possible abnormal or normal condition, such as an abnormal medical pathology. For example, in the case of a human target, the analyte(s) can include, but is not limited to, one or more of glucose, blood glucose, ketones, C-reactive proteins; blood alcohol, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The sensor systems described herein operate by transmitting an electromagnetic signal (whether in the radio or microwave frequency range of the electromagnetic spectrum in FIGS. 1-5 and 9-12 or in the visible range of the electromagnetic spectrum in FIGS. 6-8) toward and into a target using a transmit element such as a transmit antenna or a transmit LED. A returning signal that results from the transmission of the transmitted signal is detected by a receive element such as a receive antenna or a photodetector. The signal(s) detected by the receive element can be analyzed to detect the analyte based on the intensity of the received signal(s) and reductions in intensity at one or more frequencies where the analyte absorbs the transmitted signal.

FIGS. 1-5 illustrate a non-invasive analyte sensor system that uses two or more antennas including a transmit antenna and a receive antenna. The transmit antenna and the receive antenna can be located near the target and operated as further described herein to assist in detecting at least one analyte in the target. The transmit antenna transmits a signal, which has at least two frequencies in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

An example of detecting an analyte using a non-invasive spectroscopy sensor operating in the radio or microwave frequency range of the electromagnetic spectrum is described in WO 2019/217461, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

Referring now to FIG. 1, an embodiment of a non-invasive analyte sensor system with a non-invasive analyte sensor 5 is illustrated. The sensor 5 is depicted relative to a target 7 (in this example in the form of a human or animal) that contains an analyte of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1). In some embodiments, power can be provided from mains power, for example by plugging the sensor 5 into a wall socket via a cord connected to the sensor 5. The sensor 5 may be configured as a wearable device that is configured to be worn around the wrist (see FIG. 9), configured as a table top device (FIG. 10), used in an in vitro detector (see FIG. 11), or used in a non-human/animal version for example detection in an industrial process such as in a flowing fluid (see FIG. 12).

The transmit antenna 11 is positioned, arranged and configured to transmit a signal 21 that is in the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz. In an embodiment, the transmit circuit 15 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 13 is positioned, arranged, and configured to detect one or more electromagnetic response signals 23 that result from the transmission of the transmit signal 21 by the transmit antenna 11 into the target 7 and impinging on the analyte 9. The receive antenna 13 can be an electrode or any other suitable receiver of electromagnetic signals in the radio frequency (RF) or microwave range. In an embodiment, the receive antenna 13 is configured to detect electromagnetic signals having at least two frequencies, each of which is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19. In an embodiment, at least one of the receive circuit 17 or the controller 19 can be configured to decompose or demultiplex a complex signal, detected by the receive antenna 13, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9 and develop the analyte database. If provided, the external device 25 may be used to provide communication between the sensor 5 and the remote server 27, for example using a wired data connection or via a wireless data connection or Wi-Fi of the external device 25 to provide the connection to the remote server 27.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain ($S_{21}$) and an increased reflection at output ($S_{22}$) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal that is transmitted by the transmit antenna 11 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be less than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

FIGS. 2A-2C illustrate examples of antenna arrays 33 that can be used in the sensor system 5 and how the antenna arrays 33 can be oriented. Many orientations of the antenna arrays 33 are possible, and any orientation can be used as long as the sensor 5 can perform its primary function of sensing the analyte 9.

In FIG. 2A, the antenna array 33 includes the transmit antenna 11 and the receive antenna 13 disposed on a substrate 35 which may be substantially planar. This example depicts the array 33 disposed substantially in an X-Y plane. In this example, dimensions of the antennas 11, 13 in the X and Y-axis directions can be considered lateral dimensions, while a dimension of the antennas 11, 13 in the Z-axis direction can be considered a thickness dimension. In this example, each of the antennas 11, 13 has at least one lateral dimension (measured in the X-axis direction and/or in the Y-axis direction) that is greater than the thickness dimension thereof (in the Z-axis direction). In other words, the transmit antenna 11 and the receive antenna 13 are each relatively flat or of relatively small thickness in the Z-axis direction compared to at least one other lateral dimension measured in the X-axis direction and/or in the Y-axis direction.

In use of the embodiment in FIG. 2A, the sensor and the array 33 may be positioned relative to the target 7 such that the target 7 is below the array 33 in the Z-axis direction or above the array 33 in the Z-axis direction whereby one of the faces of the antennas 11, 13 face toward the target 7. Alternatively, the target 7 can be positioned to the left or right sides of the array 33 in the X-axis direction whereby one of the ends of each one of the antennas 11, 13 face toward the target 7. Alternatively, the target 7 can be positioned to the sides of the array 33 in the Y-axis direction whereby one of the sides of each one of the antennas 11, 13 face toward the target 7.

The sensor 5 can also be provided with one or more additional antenna arrays in addition the antenna array 33. For example, FIG. 2A also depicts an optional second antenna array 33a that includes the transmit antenna 11 and the receive antenna 13 disposed on a substrate 35a which may be substantially planar. Like the array 33, the array 33a may also be disposed substantially in the X-Y plane, with the arrays 33, 33a spaced from one another in the X-axis direction.

In FIG. 2B, the antenna array 33 is depicted as being disposed substantially in the Y-Z plane. In this example, dimensions of the antennas 11, 13 in the Y and Z-axis directions can be considered lateral dimensions, while a dimension of the antennas 11, 13 in the X-axis direction can be considered a thickness dimension. In this example, each of the antennas 11, 13 has at least one lateral dimension (measured in the Y-axis direction and/or in the Z-axis direction) that is greater than the thickness dimension thereof (in the X-axis direction). In other words, the transmit antenna 11 and the receive antenna 13 are each relatively flat or of relatively small thickness in the X-axis direction compared to at least one other lateral dimension measured in the Y-axis direction and/or in the Z-axis direction.

In use of the embodiment in FIG. 2B, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned in front of or behind the array 33 in the X-axis direction whereby one of the faces of each one of the antennas 11, 13 face toward the target 7. Alternatively, the target 7 can be positioned to one of the sides of the array 33 in the Y-axis direction whereby one of the sides of each one of the antennas 11, 13 face toward the target 7.

In FIG. 2C, the antenna array 33 is depicted as being disposed substantially in the X-Z plane. In this example, dimensions of the antennas 11, 13 in the X and Z-axis directions can be considered lateral dimensions, while a dimension of the antennas 11, 13 in the Y-axis direction can be considered a thickness dimension. In this example, each of the antennas 11, 13 has at least one lateral dimension (measured in the X-axis direction and/or in the Z-axis direction) that is greater than the thickness dimension thereof (in the Y-axis direction). In other words, the transmit antenna 11 and the receive antenna 13 are each relatively flat or of relatively small thickness in the Y-axis direction compared to at least one other lateral dimension measured in the X-axis direction and/or in the Z-axis direction.

In use of the embodiment in FIG. 2C, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned to the left or right sides of the array 33 in the X-axis direction whereby one of the sides of each one of the antennas 11, 13 face toward the target 7. Alternatively, the target 7 can be positioned in front of or in back of the array 33 in the Y-axis direction whereby one of the faces of each one of the antennas 11, 13 face toward the target 7.

The arrays 33, 33a in FIGS. 2A-2C need not be oriented entirely within a plane such as the X-Y plane, the Y-Z plane or the X-Z plane. Instead, the arrays 33, 33a can be disposed at angles to the X-Y plane, the Y-Z plane and the X-Z plane.

Decoupling Antennas Using Differences in Antenna Geometries

As mentioned above, one technique for decoupling the transmit antenna 11 from the receive antenna 13 is to intentionally configure the transmit antenna 11 and the receive antenna 13 to have intentionally different geometries. Intentionally different geometries refers to differences in geometric configurations of the transmit and receive antennas 11, 13 that are intentional, and is distinct from differences in geometry of the transmit and receive antennas 11, 13 that may occur by accident or unintentionally, for example due to manufacturing errors or tolerances when fabricating the antennas 11, 13.

The different geometries of the antennas 11, 13 may manifest itself, and may be described, in a number of different ways. For example, in a plan view of each of the antennas 11, 13 (such as in FIGS. 3A-C), the shapes of the perimeter edges of the antennas 11, 13 may be different from one another. The different geometries may result in the antennas 11, 13 having different surface areas in plan view. The different geometries may result in the antennas 11, 13 having different aspect ratios in plan view (i.e. a ratio of their sizes in different dimensions; for example, as discussed in further detail below, the ratio of the length divided by the width of the antenna 11 may be different than the ratio of the length divided by the width for the antenna 13). In some embodiments, the different geometries may result in the antennas 11, 13 having any combination of different perimeter edge shapes in plan view, different surface areas in plan view, and/or different aspect ratios. In some embodiments, the antennas 11, 13 may have one or more holes formed therein (see FIG. 2B) within the perimeter edge boundary, or one or more notches formed in the perimeter edge (see FIG. 2B).

So as used herein, a difference in geometry or a difference in geometrical shape of the antennas 11, 13 refers to any intentional difference in the figure, length, width, size, shape, area closed by a boundary (i.e. the perimeter edge), etc. when the respective antenna 11, 13 is viewed in a plan view.

The antennas 11, 13 can have any configuration and can be formed from any suitable material that allows them to perform the functions of the antennas 11, 13 as described herein. In one embodiment, the antennas 11, 13 can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 3A-C). A strip of material can include a wire. The antennas 11, 13 can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive.

Figure 3A:
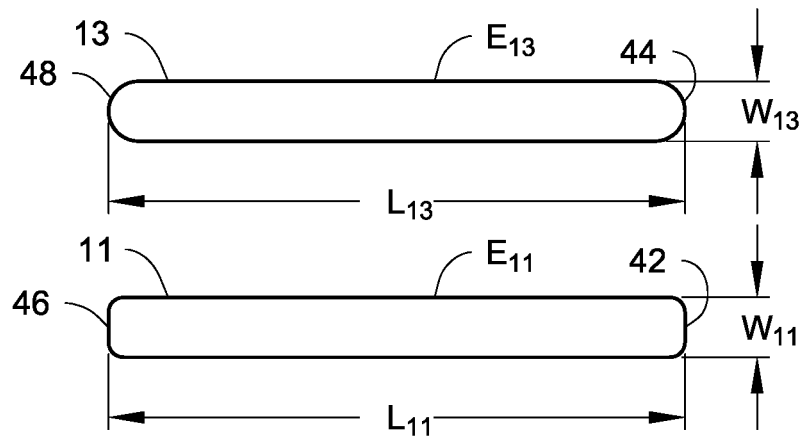
FIGS. 3A-3C illustrate different examples of transmit and receive antennas with different geometries.
Figure 3B:
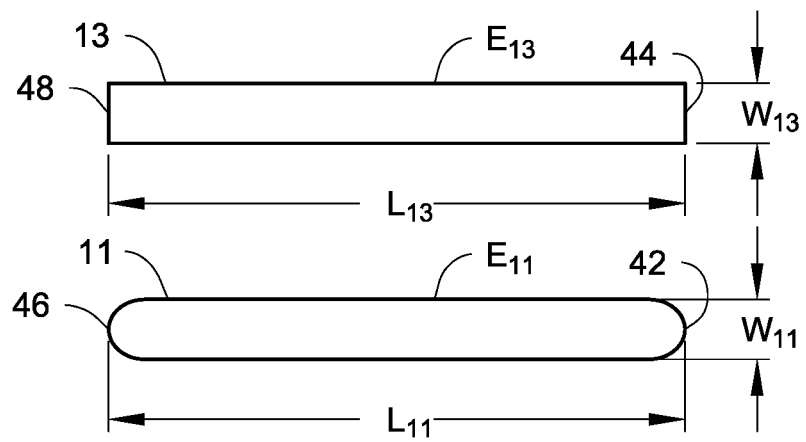
Figure 3C:
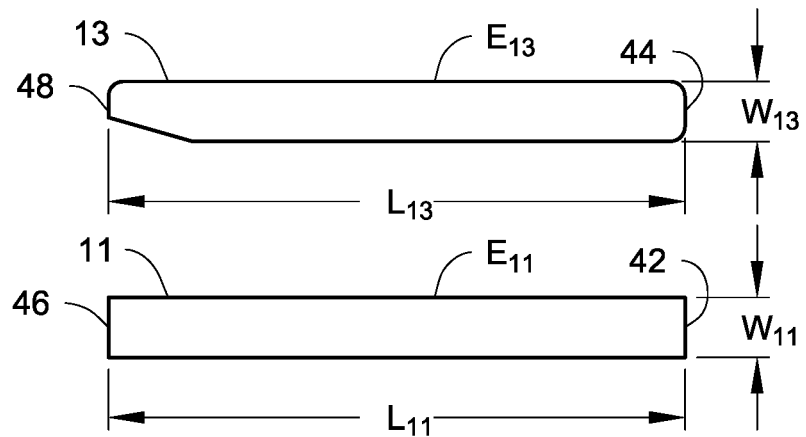

In FIGS. 2A-2C, the antennas 11, 13 within each one of the arrays 33, 33a have different geometries from one another. In addition, FIGS. 3A-C illustrate plan views of additional examples of the antennas 11, 13 having different geometries from one another. The examples in FIGS. 2A-2C and 3A-C are not exhaustive and many different configurations are possible.

FIG. 3A illustrates a plan view of an antenna array having two antennas with different geometries. In this example, the antennas 11, 13 are illustrated as substantially linear strips each with a lateral length $L_{11}$, $L_{13}$, a lateral width $W_{11}$, $W_{13}$, and a perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3A. In this example, the antennas 11, 13 differ in geometry from one another in that the shapes of the ends of the antennas 11, 13 differ from one another. For example, when viewing FIG. 3A, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. It is also possible that the lateral lengths $L_{11}$, $L_{13}$ and/or the lateral widths $W_{11}$, $W_{13}$ of the antennas 11, 13 could differ from one another.

FIG. 3B illustrates another plan view of an antenna array having two antennas with different geometries that is somewhat similar to FIG. 3A. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3B. In this example, the antennas 11, 13 differ in geometry from one another in that the shapes of the ends of the antennas 11, 13 differ from one another. For example, when viewing FIG. 3B, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

FIG. 3C illustrates another plan view of an antenna array having two antennas with different geometries that is somewhat similar to FIGS. 3A and 3B. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3C. In this example, the antennas 11, 13 differ in geometry from one another in that the shapes of the ends of the antennas 11, 13 differ from one another. For example, when viewing FIG. 3C, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 4A:
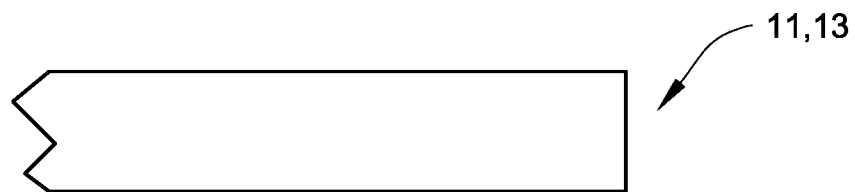
FIGS. 4A, 4B, 4C and 4D illustrate additional examples of different shapes that the ends of the transmit and receive antennas can have.
Figure 4B:
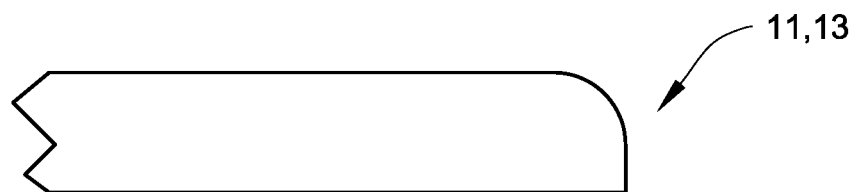
Figure 4C:
Figure 4D:
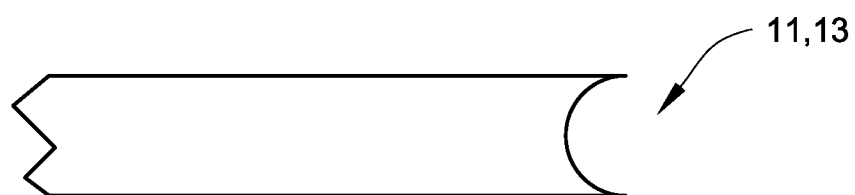

FIGS. 4A-D are plan views of additional examples of different shapes that the ends of the transmit and receive antennas 11, 13 can have to achieve differences in geometry. Either one of, or both of, the ends of the antennas 11, 13 can have the shapes in FIGS. 4A-D, including in the embodiments in FIGS. 3A-C. FIG. 4A depicts the end as being generally rectangular. FIG. 4B depicts the end as having one rounded corner while the other corner remains a right angle. FIG. 4C depicts the entire end as being rounded or outwardly convex. FIG. 4D depicts the end as being inwardly concave. Many other shapes are possible.

Figure 5:
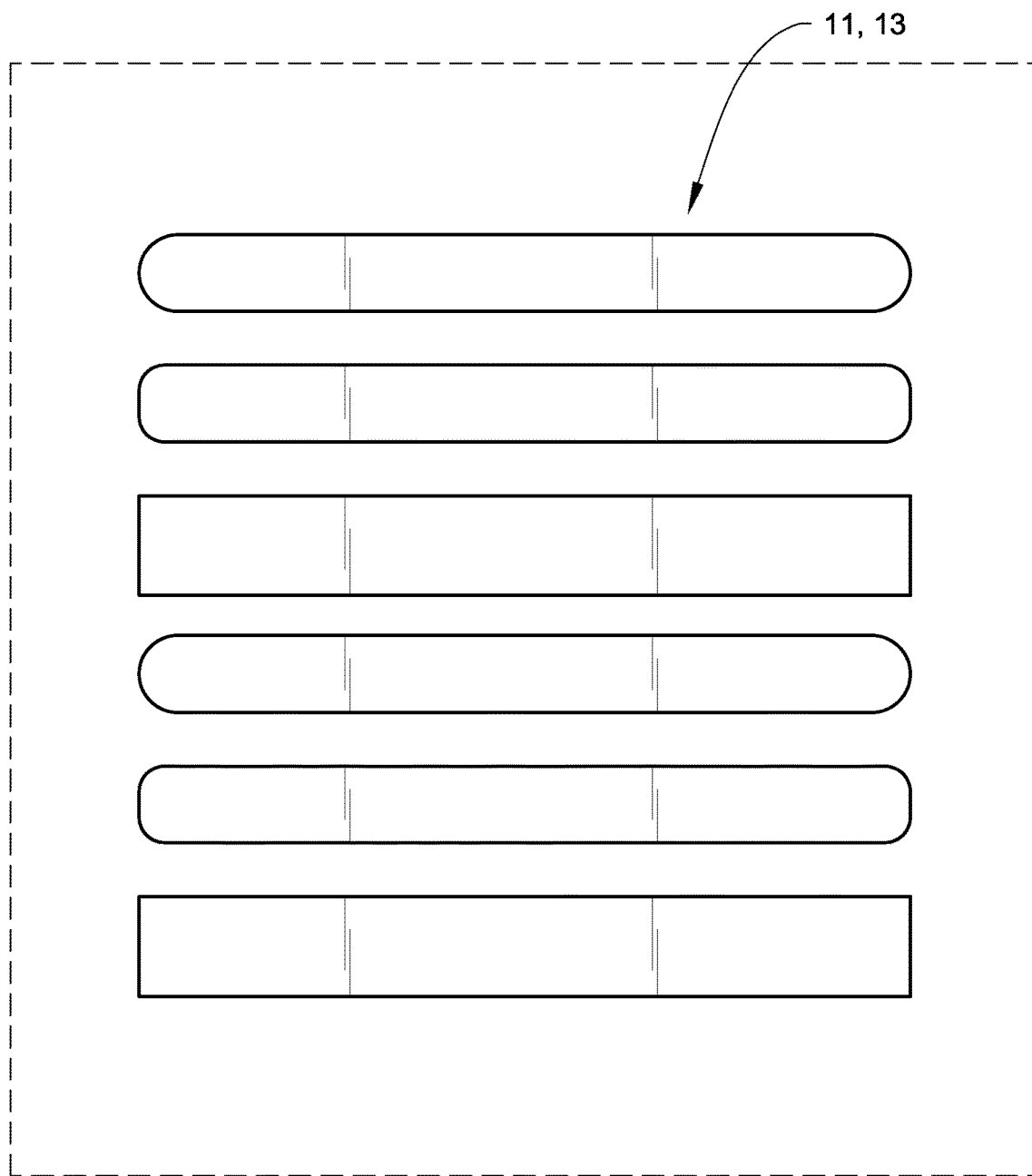
FIG. 5 illustrates another example of an antenna array that can be used.

FIG. 5 illustrates another plan view of an antenna array having six antennas illustrated as substantially linear strips. In this example, the antennas differ in geometry from one another in that the shapes of the ends of the antennas, the lateral lengths and/or the lateral widths of the antennas differ from one another.

Another technique to achieve decoupling of the antennas is to use an appropriate spacing between each antenna with the spacing being sufficient to force most or all of the signal(s) transmitted by the transmit antenna into the target, thereby minimizing the direct receipt of electromagnetic energy by the receive antenna directly from the transmit antenna. The appropriate spacing can be used by itself to achieve decoupling of the antennas. In another embodiment, the appropriate spacing can be used together with differences in geometry of the antennas to achieve decoupling.

Referring to FIG. 2A, there is a spacing D between the transmit antenna 11 and the receive antenna 13 at the location indicated. The spacing D between the antennas 11, 13 may be constant over the entire length (for example in the X-axis direction) of each antenna 11, 13, or the spacing D between the antennas 11, 13 could vary. Any spacing D can be used as long as the spacing D is sufficient to result in most or all of the signal(s) transmitted by the transmit antenna 11 reaching the target and minimizing the direct receipt of electromagnetic energy by the receive antenna 13 directly from the transmit antenna 11, thereby decoupling the antennas 11, 13 from one another.

In addition, there is preferably a maximum spacing and a minimum spacing between the transmit antenna 11 and the receive antenna 13. The maximum spacing may be dictated by the maximum size of the housing 29. In one embodiment, the maximum spacing can be about 50 mm. In one embodiment, the minimum spacing can be from about 1.0 mm to about 5.0 mm.

FIG. 9 illustrates an example use of the sensor 5 of FIG. 1 in the form of a body wearable sensor, in particular a watch-like device 90 worn around the wrist. The sensor 5 is incorporated into a sensor body 92 that is fastened to the wrist by a strap 94 that extends around the wrist.

FIG. 10 illustrates an example use of the sensor 5 of FIG. 1 in the form of a tabletop device 100. The term "tabletop" is used interchangeably with "countertop" and refers to a device that is intended to reside on a top surface of a structure such as, but not limited to, a table, counter, shelf, another device, or the like during use. In some embodiments, the device 100 can be mounted on a vertical wall. The device 100 is configured to obtain a real-time, on-demand reading of an analyte in a user such as, but not limited to, obtaining a glucose level reading of the user using the non-invasive analyte sensor 5 incorporated into the device 100. The device 100 is illustrated as being generally rectangular box shaped. However, the device 100 can have other shapes such as cylindrical, square box, triangular and many other shapes. The device 100 includes a housing 102, a reading area 104, for example on a top surface of the housing 102, where the antennas 11, 13 of the sensor 5 are positioned to be able to obtain a reading, and a display screen 106, for example on the top surface of the housing 102, for displaying data such as results of a reading by the sensor 5. Power for the device 100 can be provided via a power cord 108 that plugs into a wall socket. The device 100 may also include one or more batteries which act as a primary power source for the device 100 instead of power provided via the power cord 108 or the one or more batteries can act as a back-up power source in the event power is not available via the power cord 108. A reading by the device 100 can be triggered with a trigger button 110. An on/off power button or switch 112 can be provided anywhere on the device 100 to power the device 100 on and off. The on/off power button or switch 112 could also function as the trigger button instead of the trigger button 110. Alternatively, the trigger button 110 may act as an on/off power button to power the device 100 on and off, as well as trigger a reading.

FIG. 11 illustrates the sensor 5 of FIG. 1 incorporated into an in vitro sensor 120 that is configured to operate with an in vitro sample that is held in a sample container 122 that contains a sample to be analyzed, where the container 122 is held in a sample chamber 124. The sensor 120 can include additional features that are similar to the features of the housing disclosed in U.S. Pat. No. 9,041,920 the entire contents of which are incorporated herein by reference.

FIG. 12 illustrates the sensor 5 of FIG. 1 as an in vitro sensor 130 in an industrial process, for example with an in vitro fluid passageway 132 through which an in vitro fluid flows as indicated by the arrow A. The sensor 130 can be positioned outside the passageway 132 as illustrated, or the sensor 130 can be positioned within the passageway 132. The sensor 130 can be used in any application that can transmit the signal(s) into a target and receive a response.

FIG. 6 schematically depicts another example of a non-invasive analyte sensor 50 that forms a portion of another embodiment of a non-invasive analyte sensor system. The non-invasive analyte sensor 50 uses electromagnetic energy in the form of light waves at selected electromagnetic frequencies to perform non-invasive analyte sensing described herein. The sensor 50 includes a housing 52 and a sensor array that includes a plurality of transmit elements 54 each of which can emit electromagnetic energy in the form of light. In this example, the transmit elements 54 are disposed in an array surrounding a receive element 56 which can be a photodetector. The illustrated example depicts the array as having a total of twelve of the elements 54 arranged in a circular array around the receive element 56. However, a larger or smaller number of the elements 54 can be provided in the array. In addition, the array can have an arrangement other than being a circular array. The separate receive element 56 is not necessary if one of the elements 54 is controlled to function as a receive element as described in detail below with respect to LEDs that can function to both emit light and detect light.

FIG. 7 illustrates another embodiment similar to FIG. 6. In FIG. 7, each of the elements 54 are controlled in a manner whereby any one or more of the elements 54 can emit light (and thereby function as a transmit element) and any one or more of the elements 54 can act as a light detector (and thereby function as a receive element). In FIG. 7, since an element 54 can function as a transmit element or as a receive element, the use of a separate receive element 56 as in FIG. 6 is not required. However, the separate receive element 56 can be included if desired. The illustrated example depicts the array as having a total of twelve of the elements 54 arranged into a 3×4 or 4×3 array. However, a larger or smaller number of the elements 54 can be provided in the array. In addition, the array can have other arrangements including the elements 54 being disposed in a circular array.

In one embodiment, the elements 54 in FIGS. 6 and 7 may be light emitting diodes (LEDs) and the array that includes the LEDs can be referred to as an LED array. LEDs that can be selectively controlled to emit light (i.e. a photoemitter) or detect light (i.e. a photodetector) are known. See Stojanovic et al., An optical sensing approach based on light emitting diodes, Journal of Physics: Conference Series 76 (2007); Rossiter et al., A novel tactile sensor using a matrix of LEDs operating in both photoemitter and photodetector modes, Proc of 4th IEEE International Conference on Sensors (IEEE Sensors 2005). See also U.S. Pat. No. 4,202,000 the entire contents of which are incorporated herein by reference.

Referring to FIG. 8, in the embodiments of FIGS. 6 and 7 some or all the elements 54 may be flush with a surface 58 of the housing 52 so that light emitted by each transmit element 54 may be transmitted from the sensor 50 and receive element 56 (or one of the elements 54 acting as a receive element) detects returning light. In another embodiment, some or all of the transmit elements 54 may be recessed within the housing 52 but the light from each transit element 54 is suitably channeled to the outside and returning light suitably channeled to the receive elements 54. In still another embodiment, some or all of the transmit elements 54 may project (partially or completely) from the surface 58 of the housing 52.

In FIGS. 6 and 7, when the elements 54 are LEDs, the LEDs can be controlled in a manner whereby any one or more of the LEDs can emit light. In addition, the receive element 56 of FIG. 6 can act as a light detector, or any one or more of the LEDs in FIGS. 6 and 7 can be controlled to act as a light detector. The LEDs that are used preferably permit at least two different wavelengths of light to be emitted. In another embodiment, at least three or more different wavelengths of light can be emitted. In one embodiment, each one of the LEDs can emit a different wavelength of light. In one embodiment, two or more of the LEDs can emit the same wavelength of light. The LED's can emit wavelengths that are in the human visible spectrum (for example, about 380 to about 760 nm) including, but not limited to, wavelengths that are visibly perceived as blue light, red light, green light, white light, orange light, yellow light, and other colors, as well as emit wavelengths that are not in the human visible spectrum including, but not limited to, infrared wavelengths. Combinations of wavelengths in the visible and non-visible spectrums may also be used. The light waves emitted by the sensor 50 function in a manner similar to the RF waves emitted by the sensor 5 in FIGS. 1-5 since both are electromagnetic waves. For example, referring to FIG. 8, light waves 60 emitted by the element 54 penetrate into a target and reflect from an analyte in the target to form the returning light waves 62 which are detected, for example the receive element 56 (or by an LED acting as a receive element).

Figure 13:
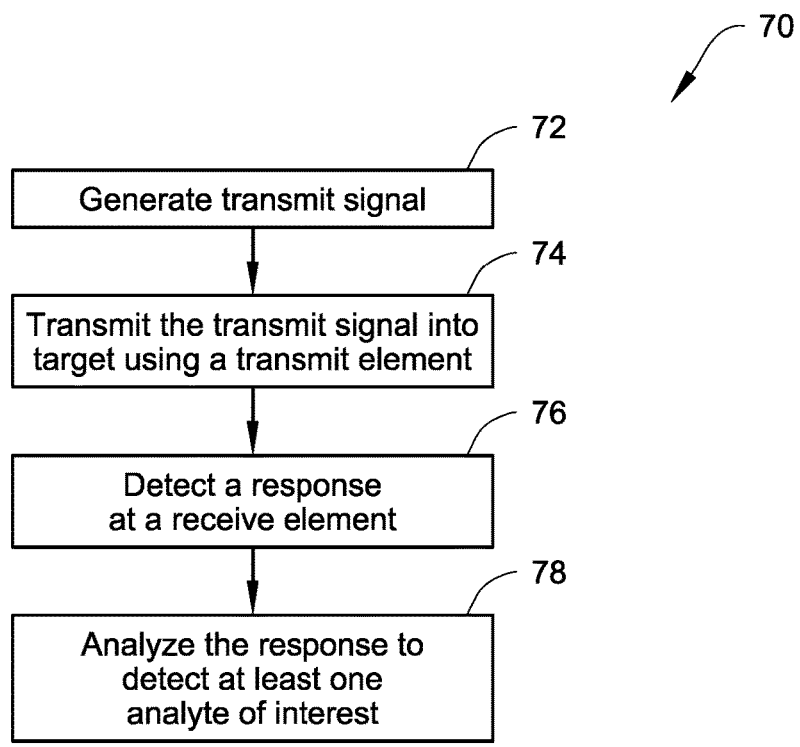
FIG. 13 is a flowchart of a method for detecting an analyte according to an embodiment.

With reference now to FIG. 13, one embodiment of a method 70 for detecting at least one analyte in a target is depicted. The method in FIG. 13 can be practiced using any of the embodiments of sensor devices described herein including the sensor 5 and the sensor 50. In order to detect the analyte, the sensor 5, 50 is placed in relatively close proximity to the target. Relatively close proximity means that the sensor 5, 50 can be close to but not in direct physical contact with the target, or alternatively the sensor 5, 50 can be placed in direct, intimate physical contact with the target. The spacing (if any) between the sensor 5, 50 and the target can be dependent upon a number of factors, such as the power of the transmitted signal. Assuming the sensor 5, 50 is properly positioned relative to the target, at box 72 the transmit signal is generated, for example by the transmit circuit 15. The transmit signal is then provided to the transmit element (11 or 54) which, at box 74, transmits the transmit signal toward and into the target. At box 76, a response resulting from the transmit signal contacting the analyte(s) is then detected by the receive element (13, 54, or 56). The receive circuit obtains the detected response from the receive element and provides the detected response to the controller. At box 78, the detected response can then be analyzed to detect at least one analyte. The analysis can be performed by the controller 19 and/or by the external device 25 and/or by the remote server 27.

Figure 14:
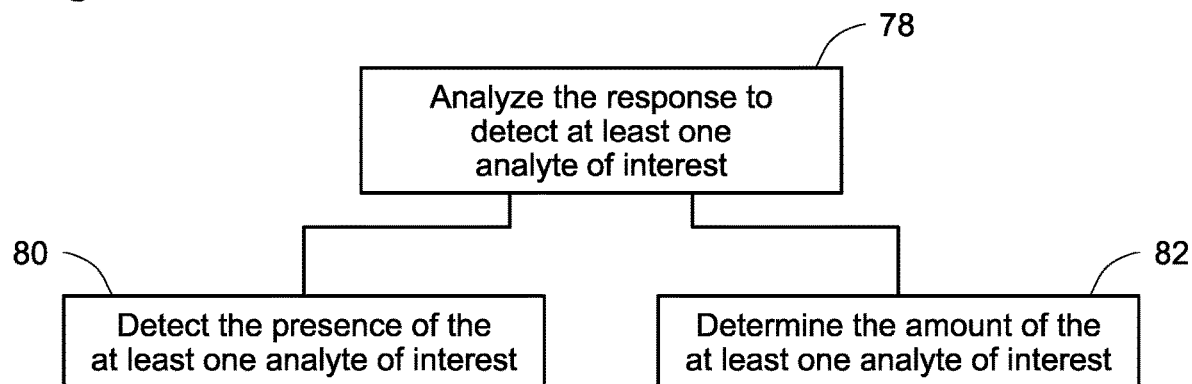
FIG. 14 is a flowchart of analysis of a response according to an embodiment.

Referring to FIG. 14, the analysis at box 78 in the method 70 can take a number of forms. In one embodiment, at box 80, the analysis can simply detect the presence of the analyte, i.e. is the analyte present in the target. Alternatively, at box 82, the analysis can determine the amount of the analyte that is present.

For example, in the case of the sensor being the sensor 5 and the signal being in the radio frequency range, the interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

In operation of either one of the sensors 5, 50 of FIGS. 1-12, one or more frequency sweeps or scan routines can implemented. The frequency sweeps can be implemented at a number of discrete frequencies (r frequency targets) over a range of frequencies. An example of a frequency sweep in a non-invasive analyte sensor using frequencies in the radio/microwave frequency range is described in WO 2019/217461, the entire contents of which are incorporated herein by reference. In the case of the sensor 50, a frequency sweep can be implemented with the sensor 50 at a number of discrete electromagnetic frequencies in the visible wavelength range over a range of electromagnetic frequencies based on the different wavelengths of the LEDs. A response spectra is detected by the receive element 56 or by the element 54 functioning as a photodetector with the response spectra being correlated to a particular analyte and analyte concentration.

In another embodiment, a non-invasive sensor can include aspects of both of the sensors 5, 50. For example, a sensor can include both two or more antennas as described herein as well as two or more of the LEDs described herein. The antennas and the LEDs can be used together to detect an analyte. In another embodiment, the antennas can be used to perform a primary detection while the LEDs can confirm the primary detection by the antennas. In another embodiment, the LEDs can be used to perform a primary detection while the antennas can be used to confirm the primary detection by the LEDs. In another embodiment, the antennas (or the LEDs) can be used to calibrate the sensor while the LEDs (or the antennas) can perform the sensing.

Figure 15:
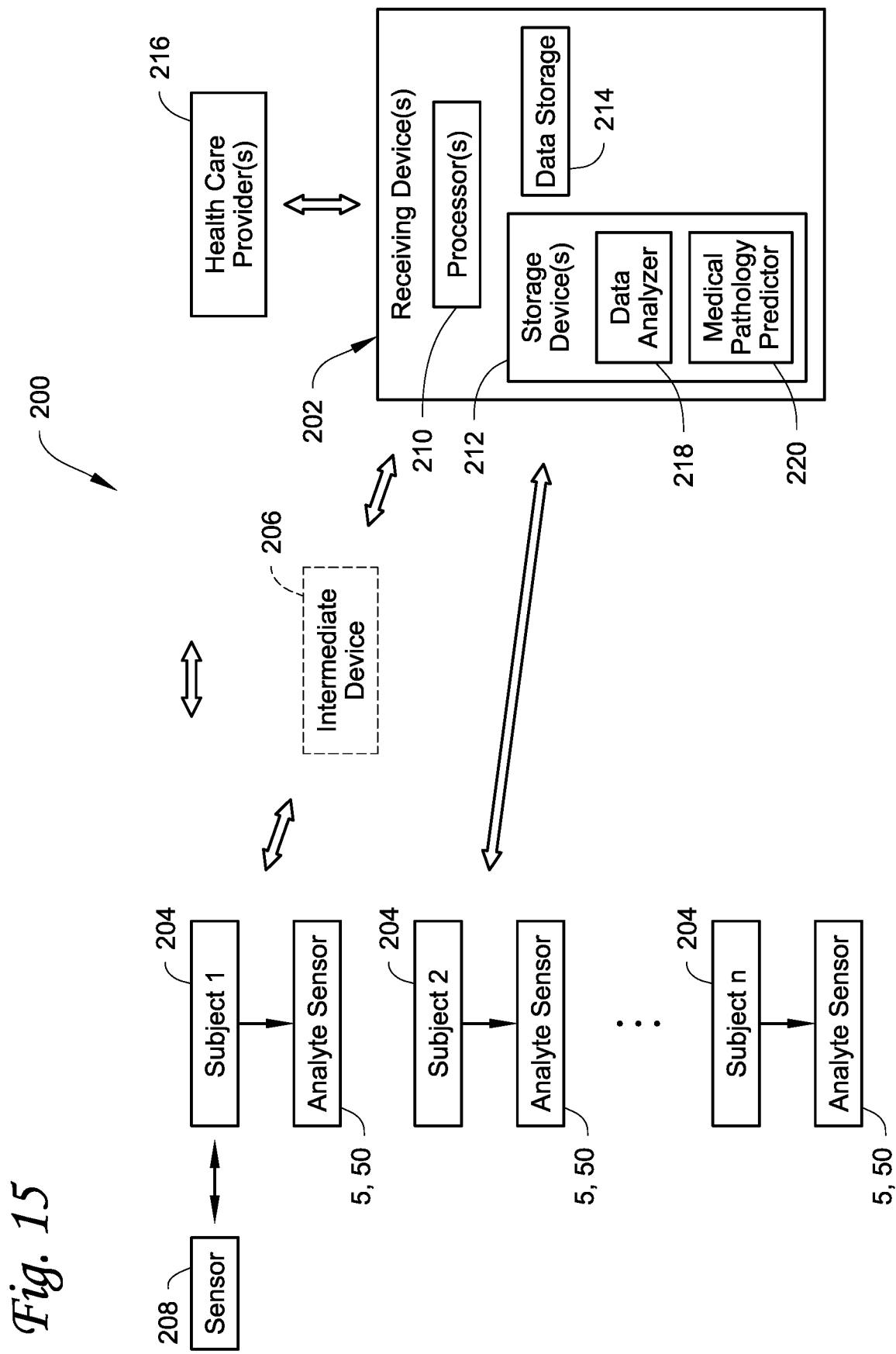
FIG. 15 is a schematic depiction of predictive medical analytics system described herein.
Figure 16:
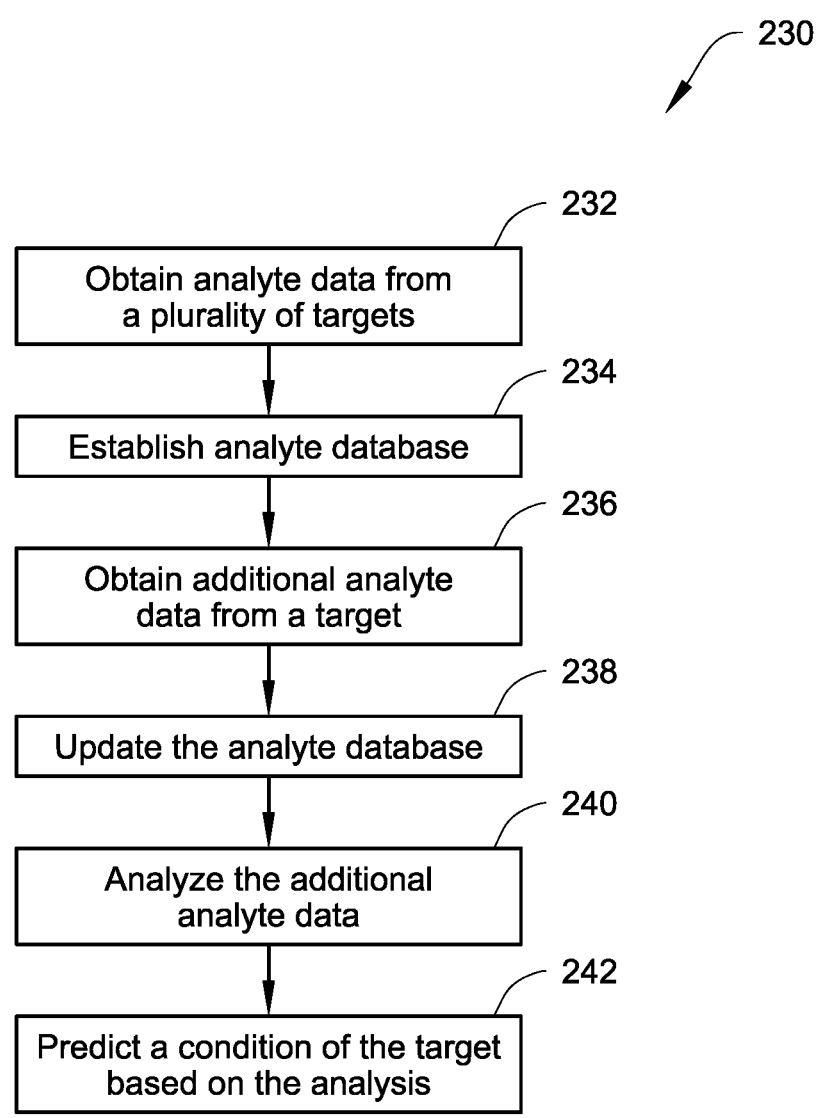
FIG. 16 is a schematic depiction of a method of establishing an analyte database and predicting a condition of a target described herein.

Referring now to FIGS. 15 and 16, systems and methods involving the use of the analyte sensors, for example similar to those described herein, to predict an actual or possible abnormal or normal condition, such as an abnormal medical condition, of a target are described. For sake of convenience, the systems and methods will be described as using the analyte sensors 5, 50 described herein with respect to FIGS. 1-12. In another embodiment, the systems and methods can use the analyte sensors disclosed in U.S. Pat. No. 10,548,503, U.S. Patent Application Publication 2019/0008422, or U.S. Patent Application Publication 2020/0187791, each of which is incorporated herein by reference in its entirety. Combinations of the features of the sensors 5, 50 described herein and disclosed in U.S. Pat. No. 10,548,503, U.S. Patent Application Publication 2019/0008422, or U.S. Patent Application Publication 2020/0187791 can be used.

Referring initially to FIG. 15, a predictive medical analytics system 200 according to one embodiment is illustrated. A similar system can be implemented with other targets. The system 200 includes a receiving device 202 that is configured to receive analyte data directly or indirectly from one or more of the analyte sensors 5, 50. Each sensor 5, 50 is interfaceable with a corresponding subject 204, for example a human or animal, for detecting at least one analyte in the subject 204. For example, the sensor 5, 50 may be worn by the subject 204, for example worn around the subjects wrist, or the sensor 5, 50 may be incorporated into a device, such as a table-top device or a hand-held device for detecting the analyte(s) in the subject 204. The sensor(s) 204 conducts a plurality of analyte sensing routines to sense at least one analyte in the subject 204, where the at least one analyte is an indicator of an abnormal medical pathology of the subject 204.

The analyte can be any analyte that is an indicator of an abnormal medical pathology due to the presence of the analyte and/or due to the concentration of the analyte. Many analytes as indicators of abnormal medical pathologies are possible, too numerous to mention. For example, the analyte can be glucose where glucose concentration levels (either high (i.e. hyperglycemia) or low (i.e. hypoglycemia)) over a period of time ae a well-known indicator of pre-diabetes or diabetes.

In another example, the analyte can be c-reactive proteins where high levels of c-reactive proteins are an indicator of diabetes, thrombotic events including myocardial infarction, and some cancers such as lung cancer and breast cancer. See Mankowski et al., "Association of C-Reactive Protein And Other Markers Of Inflammation With Risk Of Complications In Diabetic Subjects", The Journal Of The International Federation Of Clinical Chemistry And Laboratory Medicine, March 2006; Allin et al., "Elevated C-reactive protein in the diagnosis, prognosis, and cause of cancer", Crit Rev Clin Lab Sci, July-August 2011.

In another example, the analyte can be ketones where high levels of ketones are an indicator of hyperglycemia and diabetes. See Mahendran et al., Association of Ketone Body Levels With Hyperglycemia and Type 2 Diabetes in 9,398 Finnish Men", Diabetes, Vol. 62, October 2013.

In another example, the analyte can be white blood cells where high levels of white blood cells are an indicator of alcoholic liver cirrhosis. See Alcoholic Liver Cirrhosis, https://www.healthline.com/health/alcoholic-liver-cirrhosis#symptoms, September 2018.

In another example, the analyte can be luteinizing hormone (LH) where too much or too little LH can be an indicator of abnormal medical pathology including infertility, menstrual difficulties in women, low sex drive in men, and early or delayed puberty in children. See Luteinizing Hormone (LH) Levels Test, https://medlineplus.gov/lab-tests/luteinizing-hormone-lh-levels-test/#:~:text=This%20test%20measures%20the%20level, helps%20control%20the%20menstrual%20cycle.

As shown in FIG. 15, the analyte sensor 5, 50 may be in wireless or wired communication with an intermediate device 206 which in turn is in wireless or wired communication with the receiving device 202, whereby the receiving device 202 indirectly receives the analyte data from the sensor 5, 50. The intermediate device 206 can be any device that can interface with the analyte sensor 5, 50 and the receiving device 202 including, but not limited to, a mobile device such as a mobile phone, a tablet computer, a laptop computer, or the like. The intermediate device 206 may also be a personal computer. The intermediate device 206 may also be a specially designed device that is created specifically to interface with the analyte sensor 5, 50 and the receiving device 202. The intermediate device 206 may be provided with an app designed by the entity that controls the receiving device 202 that allows the intermediate device 206 to function with the analyte sensor 5, 50 and the receiving device 202. The intermediate device 206 may be owned by the subject 204, or owned by a parent if the subject 204 is a child, or owned by a care giver if the subject 204 is under care of a care giver. Alternatively or additionally, the receiving device 202 may be in direct wired or wireless communication with the analyte sensor 204 whereby the receiving device 202 directly receives the analyte data from the sensor 5, 50.

As used herein, receiving analyte data includes receiving the analyte readings from the analyte sensor 5, 50 whereby the analyte sensor 5, 50 and/or the intermediate device 206 processes the signals detected by the receive element of the sensor 5, 50 during a scan routine to determine the presence and/or concentration of the analyte, with the processed analyte data (i.e. the analyte presence and/or concentration readings) being sent to the receiving device 202. Therefore, the detected signals may be processed entirely by the analyte sensor 5, 50, the detected signals may be entirely processed by the intermediate device 206, or the detected signals may be partially processed by the analyte sensor 5, 50 and partially by the intermediate device 206. Receiving analyte data as used herein also includes receiving raw analyte readings from the analyte sensor 5, 50 and/or the intermediate device 206 whereby the raw signals detected by the receive element of the sensor 5, 50 are sent to the receive device 202 and the receive device 202 processes the raw signals to determine the presence and/or concentration of the analyte. Therefore, the detected signals may be processed entirely by the receiving device 202, or the receiving device 202 may finish processing the detected signals which have been partially processed by the analyte sensor 5, 50 and/or the intermediate device 206. In another embodiment, the receive element 202 can receive both the processed analyte data and the raw analyte data, with the receive element 202 processing the raw data to determine the presence and/or concentration of the analyte for comparison to the received processed analyte data.

The analyte data is collected by the sensor 5, 50 over a period of time that is sufficient to indicate an actual or possible abnormal medical pathology or condition of the subject 204. The time period over which the analyte data is collected may vary based on a number of factors including, but not limited to, the subject 204, the analyte being detected, temporal factors (for example time of day, the day(s) of the week, month or year), and other factors. The time period over which the analyte data is collected can be measured in minutes, hours, days, months or even years. In one embodiment, the time period can be selected to minimize or avoid collecting analyte data encompassing natural or non-abnormal variations in the analyte of the subject 204 that may occur and that may not indicate an actual or possible abnormal medical pathology of the subject 204. In another embodiment, to err on the side of medical caution, the time period that is selected may include collecting analyte data that encompasses natural or normal variations in the analyte of the subject 204 that may occur whether or not all of the collected analyte data indicates an actual or possible abnormal medical pathology. For example, the plurality of analyte sensing routines can be conducted over a period of time of at least twenty four hours, 5 days, 1 week, 1 month, 3 months, 6 months, 9 months, 1 year, and may others. In still another embodiment, instead of collecting analyte data over a period of time, a single analyte reading can be used to predict an actual or possible abnormal medical pathology.

The scan routines conducted by the analyte sensor 5, 50 to obtain the analyte data can occur continuously over the time period, or at regular or irregular intervals over the time period. The scan routines can be conducted automatically under control of a control system. In another embodiment, the scan routines can be manually triggered by the subject 204. In still another embodiment, the scan routines can be conducted automatically with the subject 204 also able to trigger one or more manual scan routines upon demand.

The analyte data can be transmitted to and received by the receiving device 202 in multiple transmissions. For example, the analyte data collected by the analyte sensor 5, 50 can be transmitted to the receiving device 202 during or after each sensing routine over the sensing period. In another embodiment, the analyte data can be transmitted to and received by the receiving device 202 in a single transmission. For example, the sensor 5, 50 or the intermediate device 206 can store the analyte data from each scan routine and at the end of the sensing period, all of the analyte data from all of the scan routines can be transmitted to the receiving device 202.

In an embodiment, a second sensor 208 can be interfaceable with the subject 204 to detect second data of the subject 204 which is transmitted to the receiving device 202. The second sensor 208 can be a second analyte sensor 5, 50 that can detect the same or different analyte as the sensor 5, 50, or the second sensor 208 can be a sensor that detects another variable of the subject 204 such as, but not limited to, heart rate, blood pressure, oxygen level, temperature, hydration, and others. The data from the second sensor 208 can be used together with the analyte data from the sensor 5, 50 to predict the abnormal medical pathology of the subject 204.

The receiving device 202 includes one or more processors 210, one or more non-transitory machine/computer-readable storage mediums (i.e. storage device(s)) 212, and one or more data storage 214. The receiving device 202 may be a server or other computer hardware. The receiving device 202 may also be implemented in a cloud computing environment.

The processor(s) 210 can have any construction that is suitable for processing the analyte data received by the receiving device 202. The processor(s) 210 can be a microprocessor, microcontroller, embedded processor, a digital signal processor, or any other type of logic circuitry. The processor(s) 210 can be single core or multi-core.

The data storage 214 stores the analyte data received by the receiving device 202 and also stores the results of the data analysis performed by the receiving device 202. The data storage 214 may also store an analyte database that is established from analyte readings obtained from the subjects 204 over a period of time. The data storage 214 can be any form of long term data storage. The data storage 214 may be implemented by cloud storage, or by data storage at a single location.

The at least one storage device 212 comprises program instructions that are executable by the one or more processors 210 to configure the receiving device 202 to be able to receive the analyte data, to transmit data and/or commands to the analyte sensor 5, 50 and/or to the intermediate device 206, and optionally to communicate with one or more health care providers 216. The health care provider 216 can be the health care provider for the subject 204, for example a nurse, a doctor or other health care provider. The program instructions of the at least one storage device 212 can further control other functions of the receiving device 202 including general operation of the receiving device 202, including internal and external communications, and interactions between the various elements of the receiving device 202, and the like.

The at least one storage device 212 can further comprise program instructions that are executable by the one or more processors 210 to function as a data analyzer 218 that analyzes the analyte data received from the sensor 5, 50 and/or from the intermediate device 206. The data analyzer 218 functions to analyze the received analyte data to determine the presence of the analyte(s) and/or the concentration of the analyte(s) in the manner described above.

The at least one storage device 212 can further comprise program instructions that are executable by the one or more processors 210 to function as a medical pathology predictor 220 that uses the results of the analysis of the analyte data to predict an abnormal medical condition of the subject 204. For example, the medical pathology predictor 220 can use the analyte data to detect trends in the analyte suggesting an actual or possible abnormal medical condition. For example, the mere presence of an analyte can indicate a possible or actual abnormal medical condition. In another example, a detected analyte level over a certain threshold, or below a certain threshold, for a period of time can be suggestive of an actual or possible abnormal medical condition. In another example, significant changes in the analyte level can be suggestive of an actual or possible abnormal medical condition.

The receiving device 202 can generate an electronic report based on the results of the analysis of the received analyte data. The report can include the results of the analysis, including a positive or normal analysis (i.e. no abnormal medical pathology exists), or including a predicted abnormal medical pathology. In the case of a predicted abnormal medical pathology, the report may also include guidance to the subject 204 on how to rectify the abnormal medical pathology, or guidance to seek medical attention to confirm and address the abnormal medical pathology, or other guidance. The receiving device 202 may include a display that displays the report, or the receiving device 202 may transmit the electronic report to a location remote from the receiving device 202. For example, the electronic report may be transmitted to the intermediate device 206 and/or to the analyte sensor 5, 50 for display. The electronic report may be transmitted to the health care provider(s) 216 who in turn may provide the report to the subject 204 or otherwise report the results to the subject 204.

In one embodiment, all of the elements of the system 200, including the analyte sensor 5, 50, the intermediate device 206 and the receiving device 202 may be provided from and controlled by a single entity. Or the entity may provide and control the analyte sensor 5, 50 and the receiving device 202, and provide an app for downloading by the subject 204 onto the intermediate device 206, for example a mobile phone or tablet owned by the subject 204, that configures the intermediate device to function with the analyte sensor 5, 50 and the intermediate device 202. Or the entity may provide and control the receiving device 202, and provide an app(s) for downloading by the subject 204 onto the intermediate device 206, for example a mobile phone or tablet owned by the subject 204 and for downloading onto the analyte sensor 5, 50, for example in the form of a smartwatch-like device owned by the subject 204, that configures the intermediate device 206 and the analyte sensor 5, 50 to function with the intermediate device 202.

A method 230 using the predictive medical analytics system 200 of FIG. 15 is illustrated in FIG. 16. The method 230 includes, at step 232, obtaining analyte data from a plurality of targets (such as the targets 204 in FIG. 15). The analyte data is obtained over a period of time, for example at least 24 hours, from each target as described herein using the analyte sensors described herein. For example, the analyte data can be sent to the receiving device 202 from the intermediate devices 206 which receive the analyte data from the analyte sensors 5, 50. The analyte data can be sent to the receiving device 202 in multiple transmissions or in a single transmission. In addition, the analyte data can be raw, unprocessed analyte data, or the analyte data can be processed data that has been processed by the intermediate device 206 and/or by the analyte sensor 5, 50.

At step 234, the analyte database is established based on the analyte data that has been obtained from the targets. The analyte data in the analyte database provides information on one or more analytes in the analyte data. For example, in the case of analyte data from human targets, the analyte data can indicate the presence and concentration of an analyte such as glucose as previously described herein. The use of analyte data from multiple targets over a prolonged period of time helps increase the confidence that the obtained data is accurate and reduces the impact of random variations in analyte levels in the targets.

Once the analyte database is established, at step 236 new or additional analyte data can be obtained from a target using one of the analyte sensors described herein. The new analyte data is obtained from the target over a period of time, for example 24 hours or more. The target can be one of the targets used to establish the analyte database, or the target can be a new target that is different from the targets used to establish the analyte database. In step 238, the new analyte data can optionally be added to the analyte database to update the analyte database.

In step 240, the new analyte data is analyzed based on the analyte database. For example, the new analyte data can be analyzed, for example using the medical pathology predictor 220 of FIG. 15, by comparing the new analyte data to the analyte data in the analyte database to determine the presence (or absence) of one or more analytes and/or determine a concentration of the one or more analytes using the analyte database. At step 242, an actual or possible condition of the target can then be predicted based on the analysis of the new analyte data. For example, if the analysis reveals the presence of a particular analyte in the new analyte data, or reveals a particular concentration of a particular analyte, that can be an indicator of an abnormal (or normal) condition, such as an abnormal medical pathology of a human target.

Figure 17:
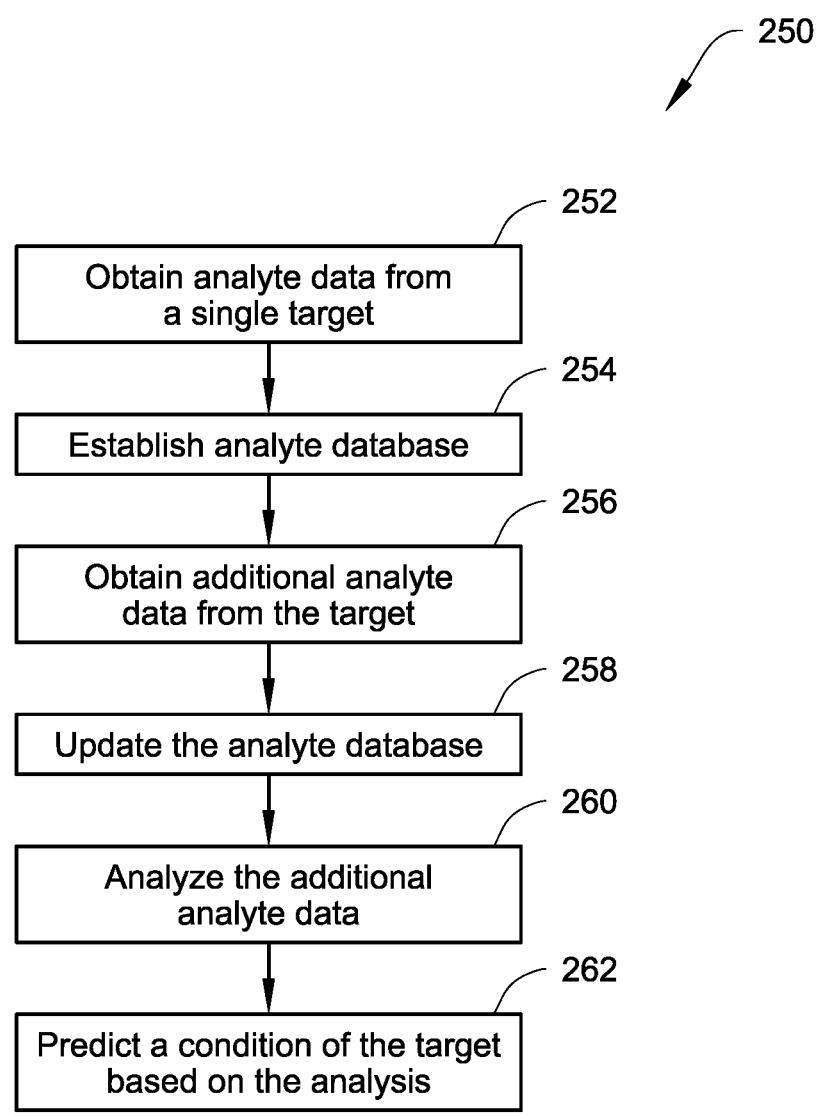
FIG. 17 is a schematic depiction of a method of establishing an analyte database using analyte data from a single target.

FIG. 17 illustrates another example of a method 250 of using the predictive medical analytics system 200 of FIG. 15. In this example, an analyte database that is specific to a single individual is established. The method 250 includes, at step 252, obtaining analyte data from a single target (such as one of the targets 204 in FIG. 15). The analyte data is obtained over a period of time, for example at least 24 hours, from the target as described herein using one or more of the analyte sensors described herein. For example, the analyte data can be sent to the receiving device 202 from the intermediate devices 206 which receive the analyte data from the analyte sensor 5, 50. The analyte data can be sent to the receiving device 202 in multiple transmissions or in a single transmission. In addition, the analyte data can be raw, unprocessed analyte data, or the analyte data can be processed data that has been processed by the intermediate device 206 and/or by the analyte sensor 5, 50.

At step 254, the analyte database is established based on the analyte data that has been obtained from the single target. The analyte data in the analyte database provides information on one or more analytes in the analyte data. For example, in the case of analyte data from a human target, the analyte data can indicate the presence and concentration of an analyte such as glucose as previously described herein. The use of analyte data from the single target over a prolonged period of time helps increase the confidence that the obtained data is accurate and reduces the impact of random variations in analyte levels in the target.

Once the analyte database is established, at step 256 new or additional analyte data can be obtained from the target using one of the analyte sensors described herein. The new analyte data is obtained from the target over a period of time, for example 24 hours or more. In step 258, the new analyte data can optionally be added to the analyte database to update the analyte database.

In step 260, the new analyte data is analyzed based on the analyte database. For example, the new analyte data can be analyzed, for example using the medical pathology predictor 220 of FIG. 15, by comparing the new analyte data to the analyte data in the analyte database to determine the presence (or absence) of one or more analytes and/or determine a concentration of the one or more analytes using the analyte database and/or determine a change in the analyte. At step 262, an actual or possible condition of the target can then be predicted based on the analysis of the new analyte data. For example, if the analysis reveals the presence of a particular analyte in the new analyte data, or reveals a particular concentration of a particular analyte, or reveals a significant change in analyte, that can be an indicator of an abnormal (or normal) condition, such as an abnormal medical pathology of a human target.

In FIGS. 16 and 17, any one or more of the establishment of the analyte databases, updating the analyte databases, analysis of the new analyte data, and predicting a condition of the target can be performed using artificial intelligence techniques, such as using machine learning techniques. For example, artificial intelligence software can be trained to recognize different signals, that are obtained by the analyte sensors described herein, that correspond to different analytes at different frequencies. The artificial intelligence software can also be trained to correlate the recognized signals and the corresponding analyte(s) to one or more corresponding determinations, such as an abnormal medical pathology associated with the corresponding analyte(s).

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. An analytics system, comprising:
 a receiving device that includes one or more processors and at least one storage device;
 the at least one storage device comprising instructions, which when executed by the one or more processors, configure the receiving device to:
  establish an analyte database that is based on analyte data that is obtained from interstitial fluid of a target by an in vitro non-invasive analyte sensor that conducted a plurality of analyte sensing routines on the target to obtain the analyte data from the interstitial fluid of the target over a period of time, the analyte data containing information on at least one analyte in the interstitial fluid of the target, and the in vitro non-invasive analyte sensor includes:

an antenna array having at least three antennas disposed side-by-side to one another, each one of the at least three antennas comprising an elongated strip of conductive material with a longitudinal axis, each one of the at least three antennas has longitudinal ends, and the longitudinal ends of the at least three antennas differ in geometrical shape from one another, at least one of the at least three antennas is controlled to operate as a transmit antenna and at least one of the at least three antennas is controlled to operate as a receive antenna, and for each analyte sensing routine of the plurality of analyte sensing routines the transmit antenna transmits an electromagnetic transmit signal that includes at least one frequency in a range of from 10 kHz to 100 GHz into the interstitial fluid of the target and the receive antenna detects a response resulting from transmission of the electromagnetic transmit signal by the transmit antenna into the interstitial fluid of the target; a transmit circuit that is electrically connectable to the transmit antenna, the transmit circuit is configured to generate the electromagnetic transmit signal to be transmitted by the at least one transmit antenna; and a receive circuit that is electrically connectable to the receive antenna, the receive circuit is configured to receive the response detected by the receive antenna.

2. The analytics system of claim 1, further comprising the in vitro non-invasive analyte sensor, and the in vitro non-invasive analyte sensor is in direct and/or indirect communication with the receiving device.

3. The analytics system of claim 1, wherein the target is a human, an animal, animate material, or inanimate material.

4. The analytics system of claim 1, wherein the analyte data in the analyte database is raw unprocessed data obtained by the in vitro non-invasive analyte sensor, and wherein the instructions, when executed by the one or more processors, further configure the receiving device to:

analyze the raw unprocessed data using the one or more processors to generate analyzed data and store the analyzed data.

5. The analytics system of claim 1, wherein the analyte data in the analyte database is raw unprocessed data obtained by the in vitro non-invasive analyte sensor, and wherein the instructions, when executed by the one or more processors, further configure the receiving device to:

analyze the raw unprocessed data to determine the presence of the at least one analyte in the interstitial fluid and/or a concentration of the at least one analyte in the interstitial fluid.

6. The analytics system of claim 1, wherein the instructions, when executed by the one or more processors, further configure the receiving device to receive the analyte data in multiple transmissions.

7. The analytics system of claim 1, wherein the instructions, when executed by the one or more processors, further configure the receiving device to receive the analyte data in a single transmission.

* * * * *